(12) United States Patent
Kirchhoff et al.

(10) Patent No.: US 11,170,667 B2
(45) Date of Patent: Nov. 9, 2021

(54) APPARATUS, SYSTEMS, AND METHODS FOR SIMULATING LIFE-LIKE HUMAN FACIAL FEATURES/EXPRESSIONS

(71) Applicant: GAUMARD SCIENTIFIC COMPANY, INC., Miami, FL (US)

(72) Inventors: Allan R. Kirchhoff, Miami, FL (US); Roberto R. Robaina, Miami, FL (US)

(73) Assignee: GAUMARD SCIENTIFIC COMPANY, INC., Miami, FL (US)

( * ) Notice: Subject to any disclaimer, the term of this patent is extended or adjusted under 35 U.S.C. 154(b) by 441 days.

(21) Appl. No.: 16/244,433

(22) Filed: Jan. 10, 2019

(65) Prior Publication Data

US 2019/0221138 A1 Jul. 18, 2019

Related U.S. Application Data

(60) Provisional application No. 62/616,689, filed on Jan. 12, 2018.

(51) Int. Cl.
*G09B 23/30* (2006.01)
*G09B 23/32* (2006.01)
(Continued)

(52) U.S. Cl.
CPC ......... *G09B 23/32* (2013.01); *A61M 5/14228* (2013.01); *G09B 23/28* (2013.01); *G09B 23/30* (2013.01); *G09B 23/34* (2013.01)

(58) Field of Classification Search
CPC ...... G09B 23/28; G09B 23/30; G09B 23/303; A63H 3/24
(Continued)

(56) References Cited

U.S. PATENT DOCUMENTS 2,812,615 A * 11/1957 Zanca ............... A63H 3/24
446/183
2,817,845 A 12/1957 Clarke
(Continued)

FOREIGN PATENT DOCUMENTS

CA 2124293 12/1994

OTHER PUBLICATIONS

Non-Final Office Action dated Sep. 10, 2018 regarding U.S. Appl. No. 15/223,795, 9 pgs.
(Continued)

*Primary Examiner* — Kurt Fernstrom
(74) *Attorney, Agent, or Firm* — Haynes and Boone, LLP

(57) ABSTRACT

A method and apparatus according to which a patient simulator includes one or more of the following: a left eye assembly including a simulated left pupil, a simulated left eyelid, and/or a simulated left iris; a right eye assembly including a simulated right pupil, a simulated right eyelid, and/or a simulated right iris; a neck assembly including a simulated neck; a left brow assembly including a simulated left brow; a right brow assembly including a simulated right brow; a tear duct assembly including simulated left and right cheeks through which artificial pores are formed; and a mouth assembly including a simulated mouth. In various embodiments, any one, or a combination, of these assemblies may be, include, or be part of, a manikin in the form of a human face, and may therefore be activated simultaneously to realistically simulate life-like human facial features/expressions.

18 Claims, 13 Drawing Sheets

(51) Int. Cl.
*G09B 23/28* (2006.01)
*A61M 5/142* (2006.01)
*G09B 23/34* (2006.01)

(58) Field of Classification Search
USPC .................. 434/262, 267, 268, 270, 272
See application file for complete search history.

(56) References Cited

U.S. PATENT DOCUMENTS

| | | | | |
|---|---|---|---|---|
| 2,888,777 | A * | 6/1959 | Kaplan | A63H 3/24 446/183 |
| 2,907,139 | A * | 10/1959 | Rekettye | A63H 3/24 446/305 |
| 2,934,856 | A * | 5/1960 | Cohn | A63H 3/24 446/183 |
| 2,954,640 | A * | 10/1960 | Catalano | A63H 3/24 446/183 |
| 2,959,890 | A * | 11/1960 | Ostrander | A63H 3/24 446/183 |
| 3,106,040 | A * | 10/1963 | Ostrander | A63H 3/24 446/306 |
| 3,209,488 | A * | 10/1965 | Brudney | A63H 3/24 446/306 |
| 3,412,504 | A * | 11/1968 | Crosman | A63H 3/24 446/132 |
| 4,339,889 | A * | 7/1982 | Guerrero | A63H 3/24 446/305 |
| 4,900,287 | A * | 2/1990 | Fusi | A63H 3/24 446/183 |
| 5,002,514 | A * | 3/1991 | Takei | A63H 3/24 446/305 |
| 5,083,962 | A * | 1/1992 | Pracas | A63H 3/008 434/268 |
| 5,083,965 | A * | 1/1992 | Mayem | A63H 3/24 446/297 |
| 5,900,923 | A | 5/1999 | Prendergast et al. | |
| 7,113,848 | B2 | 9/2006 | Hanson | |
| 7,189,137 | B2 * | 3/2007 | Ellman | A63H 3/24 446/304 |
| 7,575,330 | B2 | 8/2009 | Allen et al. | |
| 7,841,920 | B2 * | 11/2010 | Rettberg | A63H 3/24 446/305 |
| 8,025,547 | B2 * | 9/2011 | Chan | A63H 3/24 446/180 |
| 9,987,565 | B2 * | 6/2018 | Coronas Coma | A63H 3/24 |
| 10,783,803 | B2 * | 9/2020 | Huh | G09B 23/32 |
| 2012/0086018 | A1 | 4/2012 | Yao et al. | |
| 2015/0286340 | A1 | 10/2015 | Send et al. | |
| 2016/0086517 | A1 * | 3/2016 | Gao | G09B 23/34 434/271 |
| 2017/0039894 | A1 | 2/2017 | Kirchhoff et al. | |
| 2018/0144663 | A1 | 5/2018 | Kirchhoff et al. | |

OTHER PUBLICATIONS

Final Office Action dated Mar. 22, 2019 regarding U.S. Appl. No. 15/223,795, 11 pgs.
Non-Final Office Action dated Aug. 27, 2019 regarding U.S. Appl. No. 15/223,795, 15 pgs.
Extended European Search Report issued by the European Patent Office regarding related EP application No. 19151709.3 dated Nov. 4, 2020, 5 pages.
Extended European Search Report issued by the European Patent Office regarding related application No. 19151709.3 dated Feb. 22, 2019, 8 pages.

* cited by examiner

APPARATUS, SYSTEMS, AND METHODS FOR SIMULATING LIFE-LIKE HUMAN FACIAL FEATURES/EXPRESSIONS

CROSS-REFERENCE TO RELATED APPLICATION

This application claims the benefit of the filing date of, and priority to, U.S. Application No. 62/616,689, filed Jan. 12, 2018, the entire disclosure of which is hereby incorporated herein by reference.

TECHNICAL FIELD

This disclosure is related in general to interactive education systems for teaching patient care, and, more particularly, to an interactive patient simulator including a manikin resembling a human face, both in appearance and movement, and capable of life-like human facial features and expressions.

BACKGROUND

As medical science has progressed, it has become increasingly important to provide non-human interactive formats for teaching patient care. While it is desirable to train medical personnel in patient care protocols before allowing contact with real patients, textbooks and flash cards lack the important benefits to students that can be attained from hands-on practice. On the other hand, allowing inexperienced students to perform medical procedures on actual patients that would allow for the hands-on practice cannot be considered a viable alternative because of the inherent risk to the patient. Non-human interactive devices and systems can be used to teach the skills needed to successfully identify and treat various patient conditions without putting actual patients at risk.

For example, patient care education has often been taught using medical instruments to perform patient care activity on a physical simulator, such as a manikin—a manikin may be a life-sized anatomical human model used for educational and instructional purposes. Such training devices and systems can be used by medical personnel and medical students to teach and assess competencies such as patient care, medical knowledge, practice based learning and improvement, systems based practice, professionalism, and communication. The training devices and systems can also be used by patients to learn the proper way to perform self-examinations. However, existing simulators fail to exhibit accurate symptoms and to respond appropriately to student stimuli, thereby failing to provide realistic medical training to the students. Existing simulators also fail to look and feel lifelike, which fails to improve the training process. Thus, while existing physical simulators have been adequate in many respects, they have not been adequate in all respects. As such, there is a need to provide a simulator for use in conducting patient care training sessions that overcomes the above deficiencies of existing stimulators by, for example, being even more realistic and/or including additional simulated features.

DETAILED DESCRIPTION

Figure 1:
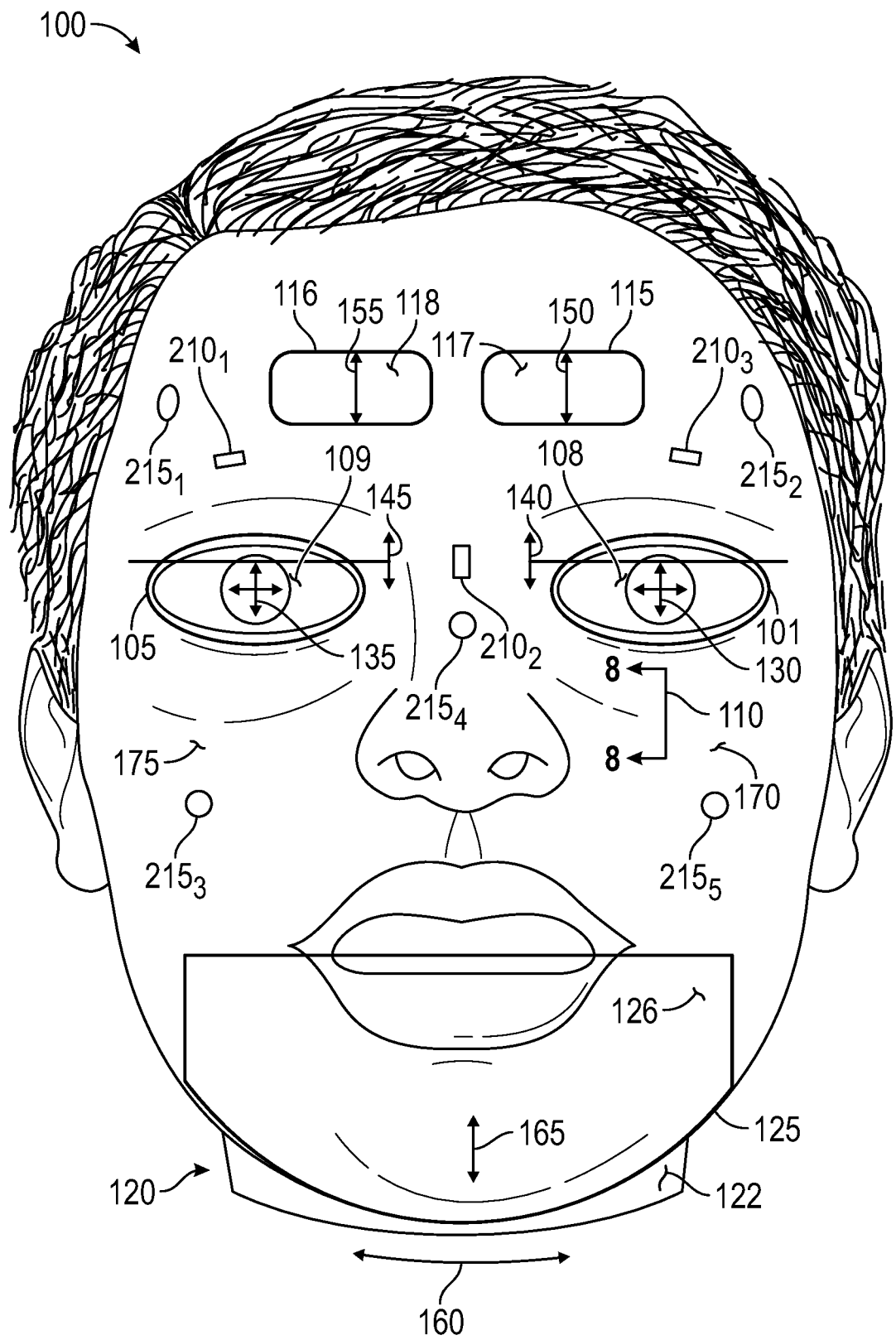
FIG. 1 is a perspective view of the manikin in the form of a human face, according to various embodiments of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

One of the aims of healthcare simulation is to establish a teaching environment that closely mimics key clinical cases in a reproducible manner. The introduction of high fidelity tetherless simulators, such as those available from Gaumard Scientific Company, Inc., over the past few years has proven to be a significant advance in creating realistic teaching environments. The present disclosure is directed to an interactive education system for teaching patient care that expands the functionality of the patient simulators by increasing the realism of the look, feel, and functionality of the patient simulators that can be used to train medical personnel in a variety of clinical situations. The interactive education system disclosed herein offers a training platform on which team-building scenarios can be performed for the development of medical treatment skills and the advancement of patient safety.

In particular, the interactive education system disclosed herein may include, or be part of, a patient simulator to provide improved realism and functionality compared to previously available simulators. Some of the various features that facilitate the improved realism and functionality are described in detail below. The interactive education system of the present disclosure allows users to practice a range of different scenarios. Thus, the interactive education system facilitates the training of a user across a broad range of simulated scenarios and corresponding assessment of the user's response to the different simulated scenarios. Accordingly, the user's medical treatment skills can be obtained and/or improved in a simulated environment without endangering a live patient.

In various embodiments, the patient simulator of the present disclosure realistically simulates the motion of a human neck, eyes, brow, mouth, and/or tear ducts in response to user stimuli in a way that replicates a live patient's clinical behavior and is therefore useful for medical educational and diagnostic purposes. To this end, the patient simulator may include neck movement and neck tracking features, which are often critical in the clinical environment because neck movement conveys important health information regarding the patient. For example, impaired neck movement may indicate that the patient has suffered from or is at risk of suffering from torticollis (i.e., a condition where the neck is stuck in a rotated position). Further, the patient simulator may include eye movement and eye tracking features, which are often critical in the clinical environment because eye movement conveys important health information regarding the patient. For example, impaired eye movement may indicate that the patient has suffered from or is at risk of suffering from a stroke, brain damage, and/or muscle damage. Further still, the patient simulator may include mouth movement features, which are often critical in the clinical environment because mouth movement conveys important health information regarding the patient. For example, impaired mouth movement may indicate that the patient has suffered from or is at risk of suffering from trismus (a condition where the mouth is unable to fully open. Finally, the patient simulator may include brow movement and/or tear duct actuation features, which are often critical in the clinical environment to evaluate a patient's behavior (e.g., the physical expression of pain) in response to a particular medical condition and/or a medical practitioner's attempts to diagnose or treat the condition.

Moreover, in various embodiments, the interactive education system allows for multiple users to simultaneously work with the patient simulator during a particular scenario, thereby facilitating team training and assessment in a realistic, team-based environment. By allowing multiple users to simultaneously interact with the interactive education system, the system facilitates the real-time training and assessment of the cooperative efforts of a team in a wide variety of scenarios, such as, by way of non-limiting example, a fire in the hospital. In various embodiments, the interactive education system provides for pre-operative care simulation as well as post-operative care simulation, thereby allowing users to experience, address, and assess pre-operative and post-operative management, including pre-operative acquisition of the patient history and management of post-operative complications.

For example, in various embodiments, the interactive education system allows for the realistic reception and transport of the patient simulator through a hospital (e.g., from an emergency room to an operating room) during operation of a particular scenario. In addition, the interactive education system can be used to conduct patient safety drills in an actual hospital or other medical setting.

In various embodiments, the interactive education system includes features designed to enhance the educational experience. For example, in various embodiments, the system includes a processing module (e.g., a microprocessor circuit or the like) to simulate different medical and/or surgical scenarios during operation of the interactive education system. In various embodiments, the system includes a camera system that allows visualization of the procedure for real-time video and log capture for debriefing purposes. In various embodiments, the interactive education system is provided with a workbook of medical scenarios that are pre-programmed in an interactive software package, thereby providing a platform on which team-building scenarios can be performed for the development of medical treatment skills and general patient safety. Thus, the interactive education system disclosed herein provides a system that is readily expandable and updatable without large expense and that enables users to learn comprehensive medical and surgical skills through "hands-on" training, without sacrificing the experience gained by users in using standard surgical instruments in a simulated patient treatment situation.

Referring initially to FIG. 1, in various embodiments, the patient simulator is, includes, or is part of, a manikin 100 in the form of a human face—the manikin 100 includes left and right eye assemblies 101 and 105 exemplified (at least in part) by ovate regions in FIG. 1, a tear duct assembly 110, left and right brow assemblies 115 and 116 exemplified (at least in part) by rounded rectangular regions in FIG. 1, a neck assembly 120, a mouth assembly 125 exemplified (at least in part) by an arch top region in FIG. 1, and associated circuitry to control functions to be performed by the various assemblies 101, 105, 110, 115, 116, 120, and 125. To simulate the realistic eye movement and eye tracking features discussed herein, the left and right eye assemblies 101 and 105 impart horizontal (left and right) and vertical (up and down) movement to both a simulated left pupil 106 (shown in FIGS. 3-5) and a simulated right pupil 107 (shown in FIGS. 3-5) of the manikin 100, as indicated in FIG. 1 by the respective 4-way arrows 130 and 135. In various embodiments, one or more components of the left and right eye assemblies 101 and 105 are substantially identical to those described in U.S. patent application Ser. No. 15/223,795, filed Jul. 29, 2016, the entire disclosure of which is hereby incorporated herein by reference. Moreover, to simulate realistic blinking features, the left and right eye assemblies 101 and 105 impart vertical (up and down) movement to both a simulated left eyelid 108 and a simulated right eyelid 109 of the manikin 100, as indicated in FIG. 1 by the respective 2-way arrows 140 and 145. Further, to simulate the realistic brow movement features discussed herein, the brow assembly 115 imparts vertical (up and down) movement to both a simulated left brow 117 and a simulated right brow 118 of the manikin 100, as indicated in FIG. 1 by the respective 2-way arrows 150 and 155. Further still, to simulate the realistic neck movement and neck tracking features discussed herein, the neck assembly 120 imparts rotational (left and right) movement to a simulated neck 122 of the manikin 100, as indicated in FIG. 1 by the 2-way arrow 160. Finally, to simulate the realistic mouth movement features discussed herein, the mouth assembly 125 imparts vertical (up and down) movement to a simulated mouth (or jaw) 126 of the manikin 100, as indicated in FIG. 1 by the 2-way arrow 165.

Figure 2:
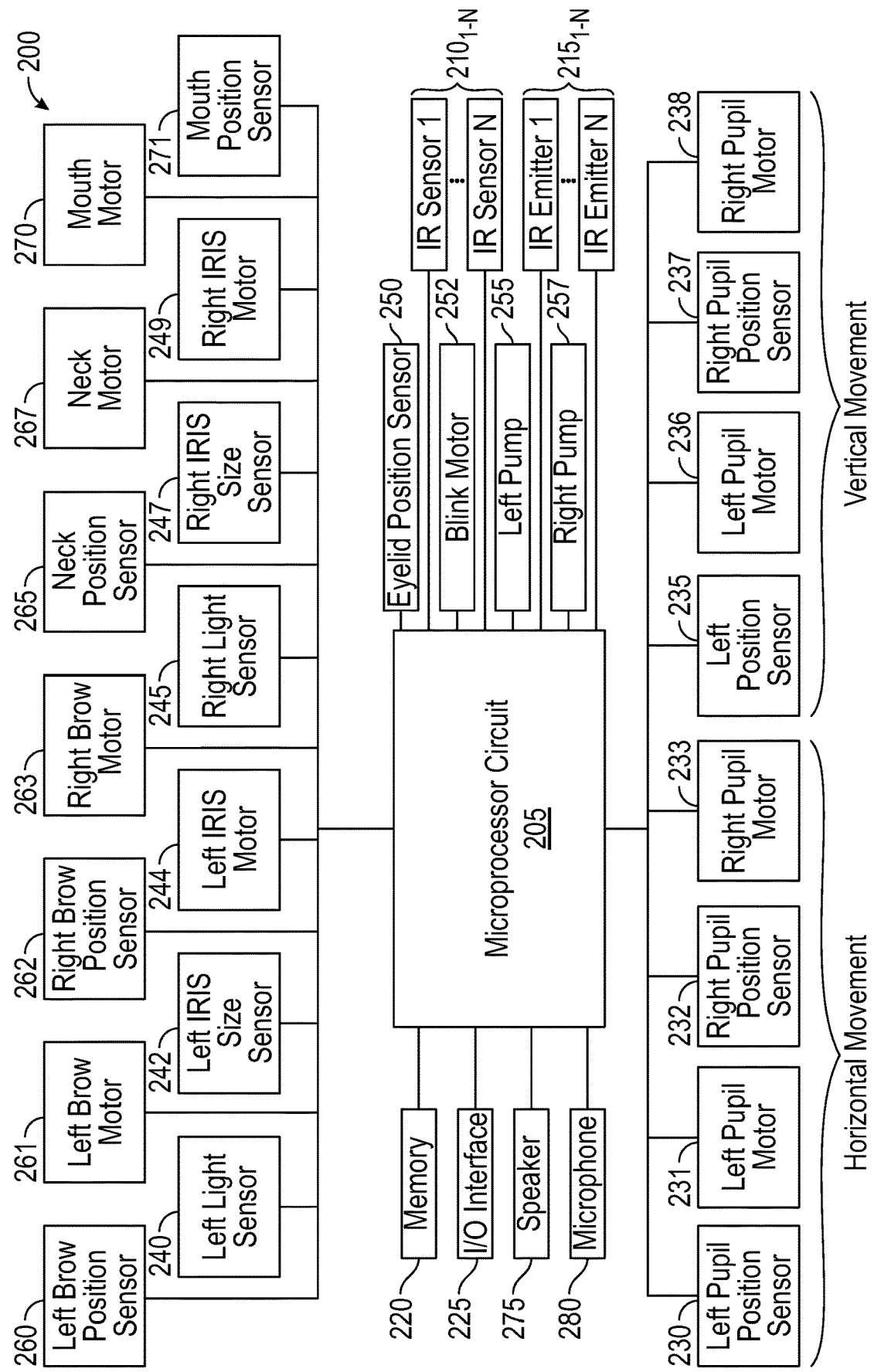
FIG. 2 is a block diagram schematically illustrating a patient simulator, which may be implemented at least in part within the environment and/or the manikin of FIG. 1, according to various embodiments of the present disclosure.

Turning also to FIG. 2, with continuing reference to FIG. 1, a block diagram of the patient simulator according to various embodiments of the present disclosure is schematically illustrated and generally referred to by the reference numeral 200. The patient simulator 200 may be implemented (at least in part) within the environment and/or the manikin 100 of FIG. 1. The patient simulator 200 includes a microprocessor circuit (or microcontroller) 205, one or more infrared ("IR") sensors $210_{1-N}$, one or more IR emitters $215_{1-N}$, an electronic memory 220, and an input/output ("I/O") interface 225. The microprocessor circuit 205 may include an integrated circuit (e.g., ASIC) and may be programmed with appropriate software to allow and enable the simulated features of the patient simulator. The I/O interface 225 may include peripheral input devices like a keyboard, mouse and joystick, and output devices such as a display, speakers, and a printer. The microprocessor circuit 205 may exchange information with connected components (internal and external) by using a Universal Serial Bus (USB), a one-wire RS-232 communication interface, or an I2C communication interface. In various embodiments, one of which is shown implemented (at least in part) within the environment and/or the manikin 100 of FIG. 1, the patient simulator includes three (3) of the IR sensors $210_{1-3}$ and five (5) of the IR emitters $215_{1-5}$. The microprocessor circuit 205 may be electrically connected to the IR emitters $215_{1-N}$, and controls operations of the IR emitters $215_{1-N}$—for example, the microprocessor circuit 205 controls the emission of IR radiation from each of the IR emitters $215_{1-N}$. Additionally, the microprocessor circuit 205 is electrically connected to the IR sensors $210_{1-N}$, and controls operation of the IR sensors $210_{1-N}$—for example, the microprocessor circuit 205 controls the sensing of reflected IR response signals by the one or more IR sensors $210_{1-N}$.

Eye Movement:

Referring still to FIG. 2, in various embodiments, to impart horizontal (left and right) movement to the simulated left pupil 106 and the simulated right pupil 107, the patient simulator 200 includes a left pupil position sensor 230, a left pupil motor 231, a right pupil position sensor 232, and a right pupil motor 233. The separate left and right pupil motors 231 and 233 allow independent control of horizontal (left and right) movement of the simulated left pupil 106 and the simulated right pupil 107, respectively. Similarly, to impart vertical (up and down) movement to the simulated left pupil 106 and the simulated right pupil 107, the patient simulator 200 includes a left pupil position sensor 235, a left pupil motor 236, a right pupil position sensor 237, and a right pupil motor 238. The separate left and right motors 236 and 238 allow independent control of vertical (up and down) movement of the simulated left pupil 106 and the simulated right pupil 107, respectively. The independent control of the simulated left pupil 106 and the simulated right pupil 107 (whether horizontal or vertical) is relevant because it allows medical tests to be performed individually on each eye. The left and right pupil position sensors 230, 232, 235, and 237 may be rotary position sensors that sense rotational positions of the simulated left and right pupils 106 and 107 respectively.

More particularly, to simulate the eye movement and eye tracking features discussed herein, the microprocessor circuit 205 instructs at least one of the IR emitters $215_{1-N}$ (i.e., the IR emitters $215_{3-5}$) to emit IR radiation and instructs at least one of the IR sensors $210_{1-N}$ (i.e., the IR sensors $210_{1-3}$) to sense the IR response signals reflected off of an approaching or passing object. The microprocessor circuit 205 may store the IR response signals sensed by the at least one of the IR sensors $210_{1-N}$ in the electronic memory 220. Based on the sensed IR response signals, the microprocessor circuit 205 determines the presence and location of the approaching or passing object. In various embodiments, the sensing of the IR response signals includes sensing an intensity of the reflected IR response signals, and recording a (digital) value corresponding to the sensed intensity of the IR response signals. The microprocessor circuit 205 may compare the recorded values, and may determine that the object is located closest to the IR sensor $210_{1-N}$ that records the greatest value. That is, the microprocessor circuit 205 may determine that the object is located closest to the IR sensor $210_{1-N}$ that senses IR response signals having the highest intensity. When two different IR sensors $210_{1-N}$ measure substantially equal IR responses, the microprocessor circuit 205 may determine that the object is located in between the two different IR sensors $210_{1-N}$. For example, the microprocessor circuit 205 may calculate a difference between two different values recorded by the two different IR sensors $210_{1-N}$, and may determine that the object is located between the two different IR sensors $210_{1-N}$ when the calculated difference is less than a predetermined threshold value. In various embodiments, the IR response may have to be equal to or greater than a predetermined threshold IR response value for the at least one IR sensor $210_{1-N}$ to sense the IR response signal.

Once the microprocessor circuit 205 has determined the location of the object with respect to the known locations of the IR sensors $210_{1-N}$, the microprocessor circuit 205 may instruct the left pupil position sensors 230 and 235 to report a current position of the simulated left pupil 106 within the left eye assembly 101, and may instruct the right pupil position sensors 232 and 237 to report a current position of the simulated right pupil 107 within the right eye assembly 105. The microprocessor circuit 205 may then independently compare the current positions of the simulated left and right pupils 106 and 107 with respect to the determined location of the object, and determine whether the current positions of the simulated left and right pupils 106 and 107 correspond to the determined location of the object. For example, to determine whether the current positions of the simulated left and right pupils 106 and 107 correspond to the determined location of the object, the microprocessor circuit 205 may determine whether the current positions of the simulated left and right pupils 106 and 107 are oriented towards the determined location of the object.

The microprocessor circuit 205 may determine to effect no change in the current positions of the simulated left and right pupils 106 and 107 when it is determined that the current positions of both the simulated left and right pupils 106 and 107 correspond to the determined location of the object. However, the microprocessor circuit 205 may instruct the left pupil motor(s) 231 and/or 236 to change the current position of the simulated left pupil 106 when it is determined that the current position of the simulated left pupil 106 does not correspond to the determined location of the object. For example, the microprocessor circuit 205 may instruct the left pupil motor(s) 231 and/or 236 to position the simulated left pupil 106 such that the simulated left pupil 106 is oriented (i.e., looking) towards the determined location of the object. Similarly, the microprocessor circuit 205 may instruct the right pupil motor(s) 233 and/or 238 to change the current position of the simulated right pupil 107 when it is determined that the current position of the simulated right pupil 107 does not correspond to the determined location of the object. For example, the microprocessor circuit 205 may instruct the right pupil motor(s) 233 and/or 238 to position the simulated right pupil 107 such that the simulated right pupil 107 is oriented (i.e., looking) towards the determined location of the object.

In various embodiments, the microprocessor circuit 205 may change the positions of the simulated left and right pupils 106 and 107 in the horizontal direction, the vertical direction, and in a combination of horizontal and vertical directions. The ability of the patient simulator 200 to effect changes in the positions of the simulated left and right pupils 106 and 107 in all of the above directions allows the patient simulator to realistically simulate various medical tests performed by doctors on human eyes. Further, the microprocessor circuit 205 may change the current position of the simulated left pupil 106 independently from the current position of the simulated right pupil 107. Further, the microprocessor circuit 205 may change the current position of the simulated left pupil 106 by an amount of displacement that is lower than, equal to, or greater than an amount of displacement of the simulated right pupil 107, and vice versa.

Figure 3:
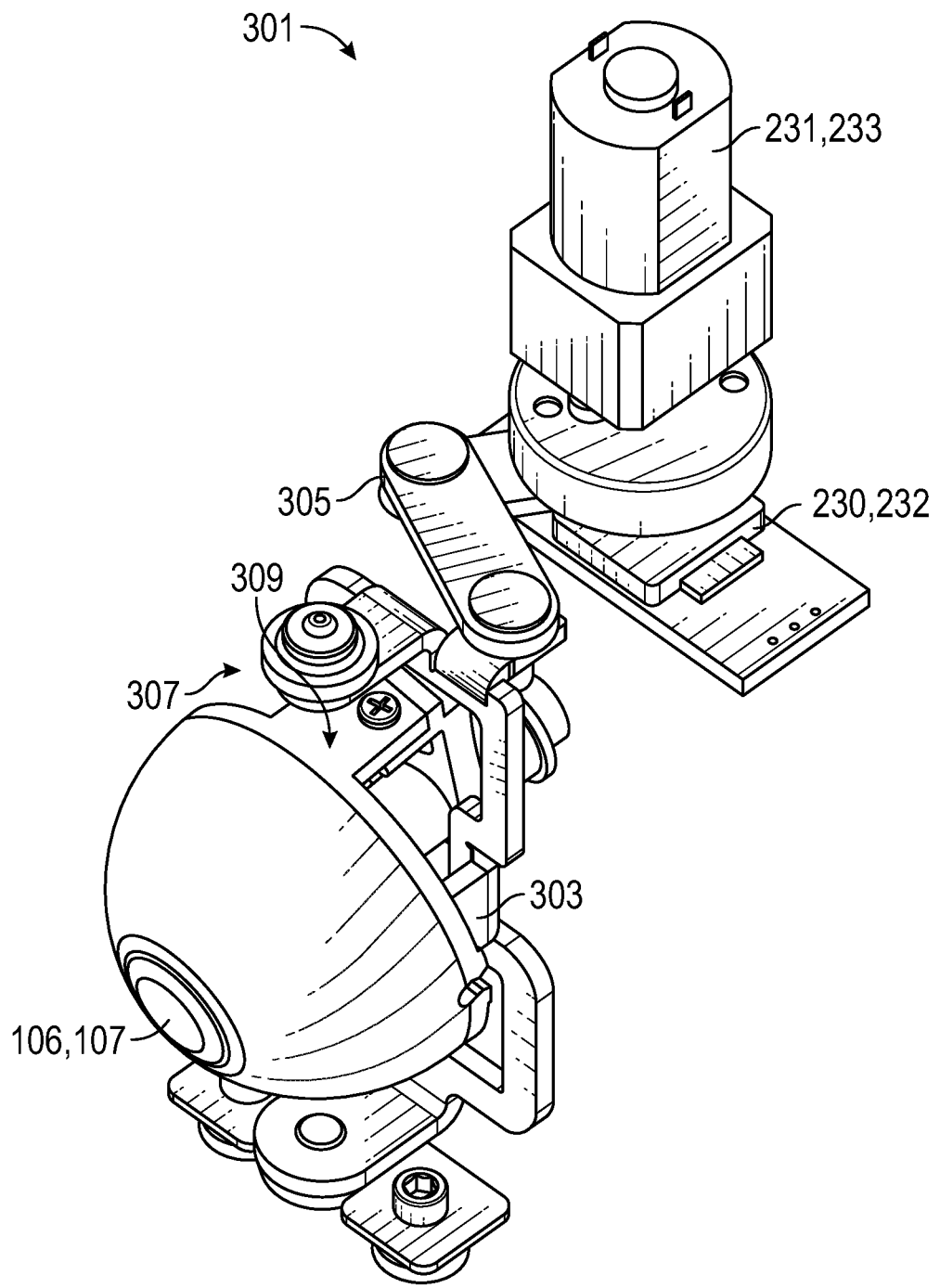
FIG. 3 is a perspective view of an apparatus for effecting horizontal movement of a left or right eye assembly, which may be implemented at least in part within the manikin, the patient simulator, and/or the respective environments of FIGS. 1 and 2, according to various embodiments of the present disclosure.
Figure 4:
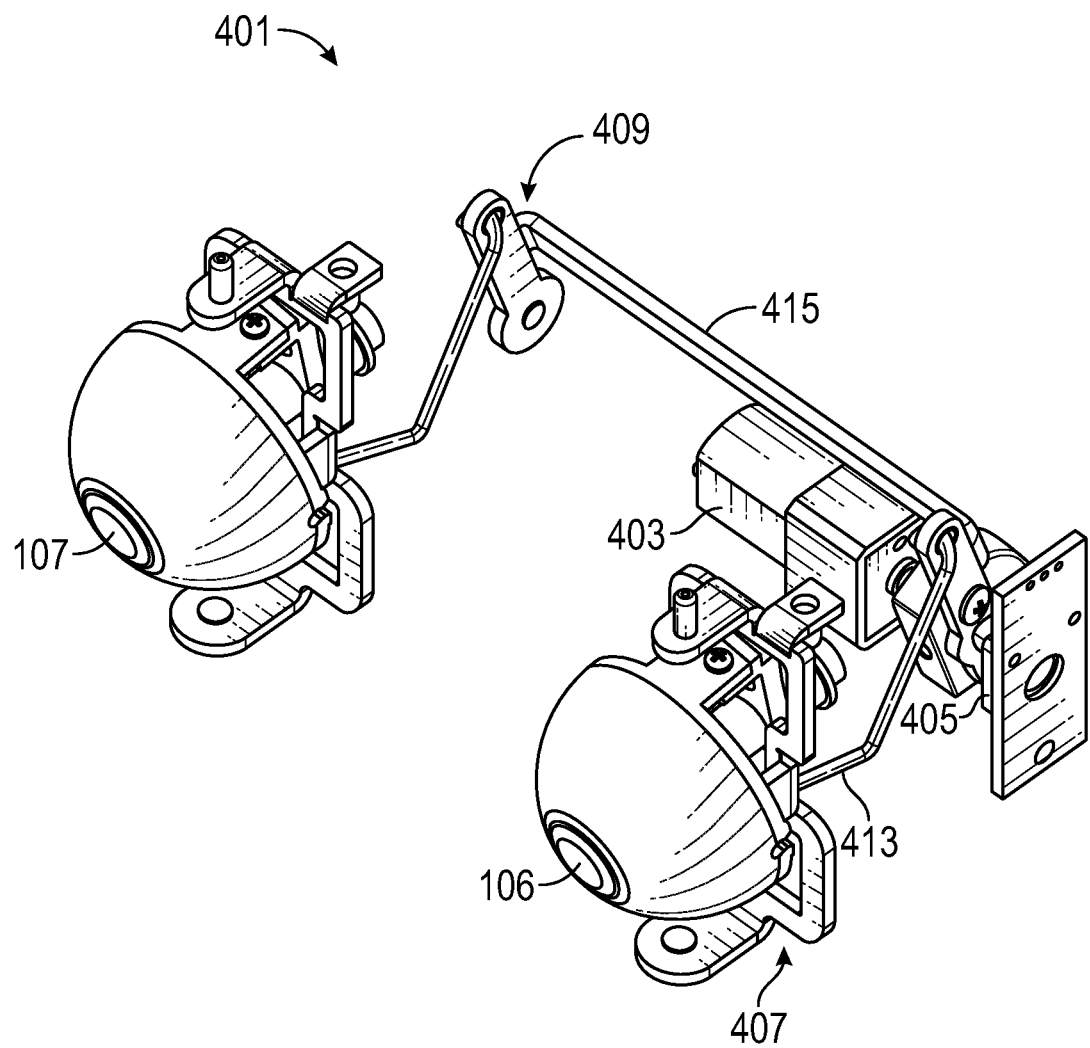
FIG. 4 is a perspective view of an apparatus for effecting vertical movement of the left and/or right eye assemblies of FIG. 3, according to various embodiments of the present disclosure.
Figure 5:
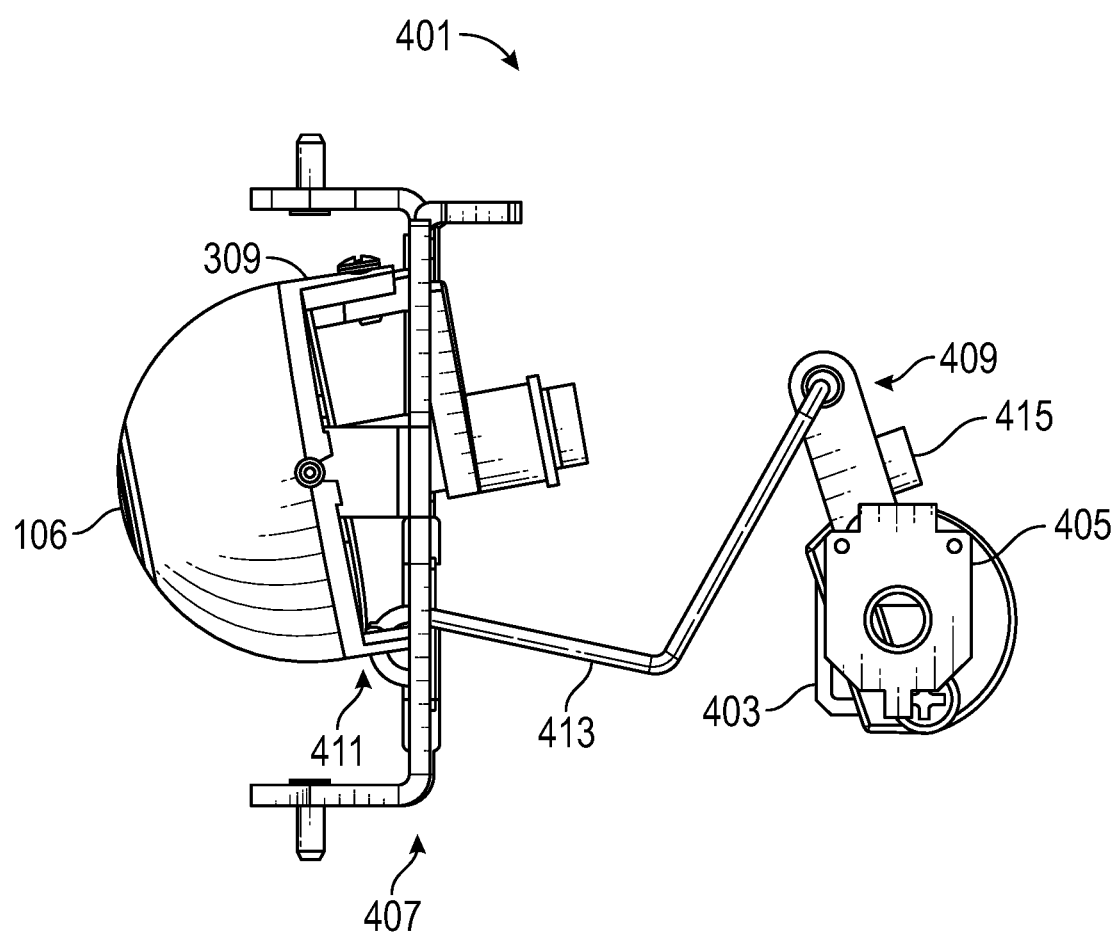
FIG. 5 is a right side elevational view of the apparatus for effecting vertical movement of the left and/or right eye assemblies of FIG. 4, according to various embodiments of the present disclosure.

Turning also to FIGS. 3-5, with continuing reference to FIGS. 1 and 2, in various embodiments, the microprocessor circuit 205 may effect changes in the positions of the simulated left and right pupils 106 and 107 to simulate horizontal movements, vertical movements, and/or a combination of horizontal and vertical movements. These movements of the simulated left and right pupils 106 and 107 in the various directions may be achieved by using a two axis gimbal, which is mounted to another rotating gimbal so that both the gimbals may rotate simultaneously to orient the pupils in any combination of horizontal and vertical rotation. This exemplary configuration of the gimbals also allows the vertical movement of the simulated left and right pupils 106 and 107 to be independent from the horizontal movement of the simulated left and right pupils 106 and 107. In various embodiments, the patient simulators according to the present disclosure may include two assemblies to effect displacement of the simulated left and right pupils 106 and 107 in the various directions. For example, simulators may include a left assembly to effect displacement of the simulated left pupil 106 and a right assembly to effect displacement of the simulated right pupil 107.

FIG. 3 illustrates an exemplary apparatus 301 used for horizontal (left and right) movement of a given pupil 106 or 107 according to various embodiments of the present disclosure—the apparatus 301 effects movement of the given pupil in the horizontal (left and right) direction. The apparatus 301 includes the pupil motor 231 or 233, the pupil position sensor 230 or 232, a gimbal 303, a lever 305, and bearings 307 for fixedly attaching the gimbal 303 to a frame 309 connected to the rear of the given pupil 106 or 107. The pupil motor 231 or 233 is electronically connected to the microprocessor circuit 205, which may instruct the pupil motor 231 or 233 to change the horizontal position of the simulated left or right pupil 106 or 107, as the case may be. Once so instructed, the pupil motor 231 or 233 rotates to effect movement of the lever 305 attached to the gimbal 303. As the lever 305 moves, the gimbal 303 rotates horizontally about an axis passing through the bearings 307. As the gimbal 303 rotates, the fixedly attached frame 309 and, therefore, the corresponding simulated pupil 106 or 107 rotates within the exemplary range of horizontal movement for the simulated left and right pupils 106 and 107. The simulated left and right pupils 106 and 107 may be controlled together or, alternatively, independently to allow simulation of eyes converging towards the nose or to exhibit diplopia.

FIGS. 4 and 5 illustrate an exemplary apparatus 401 used for vertical (up and down) movement of a given pupil 106 or 107 according to various embodiments of the present disclosure. In various embodiments, the apparatus 401 effects movement of a given pupil 106 or 107 in the vertical (up and down) direction. The apparatus 401 may include a pupil motor 403 (e.g., 236 or 238), a pupil position sensor 405 (e.g., 235 or 237), a gimbal assembly 407, a lever 409, and a frame loop 411 of the frame 309 connected to the backend of the given pupil 106 or 107. The microprocessor circuit 205 may instruct the pupil motor 403 to change the vertical position of the simulated left or right pupil 106 or 107. Once instructed, the pupil motor 403 rotates to effect movement of the gimbal assembly 407 that is attached to the lever 409. As the lever 409 moves, a crank arm 413 is moved—the crank arm 413 is curved at an end proximal to the simulated pupil 106 or 107 and is attached to the frame loop 411. The frame loop 411 is either part of the frame 309 or is fixedly attached to the frame 309. The movement of the crank arm 413 attached to the frame loop 411 rotates the pupils 106 or 107 within the exemplary range of vertical movement for the simulated left and right pupils 106 and 107.

A center at the back of the frame 309 may be connected to a center of the gimbal 303, the connection serving as a fulcrum for the vertical rotation of the simulated pupil 106 or 107. As most clearly shown in FIG. 4, the simulated left and right pupils 106 and 107 may be controlled together by using a hooked rod 415 connecting the components for both the simulated left and right pupils 106 and 107. Alternatively, the simulated left and right pupils 106 and 107 may be controlled independently to allow simulation of previously discussed vertical pupil movements. In order to make the vertical rotation of the simulated pupil 106 or 107 independent from the horizontal rotation of the simulated pupil 106 or 107, the movement of the gimbal assembly 407 should be unaffected by the horizontal rotation of the gimbal 303. This may be achieved by using the crank arm 413 that does not interfere with the horizontal rotation of the gimbal 303. The apparatus 401 also includes mechanical hard stops at both ends to ensure safe limits to the vertical rotation of the simulated left and right pupils 106 and 107.

Pupillary Change:

Pupillary change may be described as a physiological response in which the size of the iris of the pupil changes in response to light conditions sensed by the human nervous system. The change in the size of iris may be constriction or dilation. The size of the iris reduces during constriction and increases during dilation. Constriction occurs in high light (i.e., bright) conditions when the pupil allows a limited amount of light into the eye, and dilation occurs in low light (i.e., dark) conditions when the pupil allows more light into the eye. Pupillary change is an important medical indicator for healthy eyes in that healthy eyes exhibit consensual light reflex which occurs, for example, when the iris in one eye not directly stimulated reacts to stimulation of the iris in the other eye. In various embodiments, the presently disclosed simulator realistically replicates the change in size of an iris in a human eye in a way that is useful for medical educational and diagnostic purposes.

Referring back again to FIG. 2, in various embodiments, to simulate the realistic pupillary change features discussed herein, the patient simulator 200 includes the microprocessor circuit 205 electrically connected to a left light sensor 240, a left iris size sensor 242, a left iris motor 244, a right light sensor 245, a right iris size sensor 247, and a right iris motor 249 to actuate constriction or dilation. In various embodiments, the pupil dilation of each of the left and right eye assemblies 101 and 105 is controlled at least partially based on an amount of light received by the left and right light sensors 240 and 245 positioned within the eyes. That is, based on the amount of light received by the light sensors 240 and 245, the microprocessor circuit 205 activates the constriction or dilation of simulated left and right irises 601 and 603 (shown in FIG. 6) of the manikin 100. In various embodiments, the rate of change or responsiveness of the simulated left and right irises 601 and 603 can be slowed to simulate an abnormal medical condition that would result in slowed pupil constriction or dilation. In this manner, pupillary changes are simulated for medical and diagnostic purposes. Maximum sizes of the simulated left and right irises 601 and 603, and/or the rate of change or dilation of the simulated left and right irises 601 and 603 may be controlled by the microprocessor circuit 205 illustrated in FIG. 2. The simulated left and right eye assemblies 101 and 105 can be independently constricted or dilated in some instances.

In various embodiments, the left light sensor 240 senses the light conditions associated with and experienced by the left eye assembly 101, and the right light sensor 245 senses the light conditions associated with and experienced by the right eye assembly 105. Upon sensing the light conditions, the left and right light sensors 240 and 245 emit respective electrical signals to the microprocessor circuit 205 containing data/information regarding the sensed light conditions. The microprocessor circuit 205 receives the respective electrical signals, and processes the data/information regarding the sensed light conditions to determine whether to change the circular sizes of the simulated left iris 601 and/or the simulated right iris 603. In various embodiments, the microprocessor circuit 205 may determine to change the circular size of the simulated left iris 601 jointly or independently with respect to its determination whether to change the circular size of the simulated right iris 603. The microprocessor circuit 205 may send electrical signals to the left iris motor 244 and/or the right iris motor 249 to actuate the increase or decrease in the circular size of the simulate left iris 301 and/or the simulated right iris 603.

In various embodiments, to perform the simulation of realistic pupillary changes for a given eye (left or right), the given eye may be directly stimulated by subjecting it to specific lighting conditions. Upon sensing the specific light conditions, the microprocessor circuit 205 may receive electrical signals emitted from the light sensor 240 or 245 placed inside the eye in response to being subjected to the specific lighting conditions. For example, when the eye is subjected to bright lighting conditions, the light sensor 240 or 245 may emit electrical signals informing the microprocessor circuit 205 that the eye is subjected to bright light conditions, and when the eye is subjected to dark lighting conditions, the light sensor 240 or 245 emits electrical signals informing the microprocessor circuit 205 that the eye is subjected to the dark lighting conditions. Under normal lighting conditions, the light sensor 240 or 245 may emit electrical signals informing the microprocessor circuit 205 that the eyes subjected to normal lighting conditions.

Upon receiving the electrical signals, the microprocessor circuit 205 may determine whether to constrict or to dilate the simulated iris 601 or 603 of the eye. For example, when the light sensor 240 or 245 (e.g., photodiode) informs the microprocessor circuit 205 that the eye is subjected to bright lighting conditions, the microprocessor circuit 205 may determine that the simulated iris 601 or 603 of the eye should be constricted, and when the light sensor 240 or 245 informs the microprocessor circuit 205 that the eye is subjected to dark lighting conditions, the microprocessor circuit 205 may determine that the simulated iris 601 or 603 of the eye should be dilated. Based on this information, the microprocessor circuit 205 may determine a size of the simulated iris 601 or 603 to be effected. For example, the electrical signals may include information regarding and intensity of the specific lighting conditions. Based on this information, the microprocessor circuit 205 may determine a size of the simulated iris 601 or 603 to be effected to correspond to the intensity of the specific lighting conditions.

The microprocessor circuit 205 may then determine the current size of the simulated iris 601 or 603 of the eye. For example, the microprocessor circuit 205 may instruct the iris size sensor 242 or 247 for the given eye to report the current size of the simulated iris 601 or 603 of the eye. Once the microprocessor circuit 205 has determined the current size of the simulated iris 601 or 603 of the eye, the microprocessor circuit 205 compares the current size of the simulated iris 601 or 603 with the size of the simulated iris 601 or 603 to be effected. Based on the comparison of the current size and the determined size of the simulated iris 601 or 603, the microprocessor circuit 205 determines whether to change the size of the simulated iris 601 or 603. For example, if the microprocessor circuit 205 determines that the current size of the simulated iris 601 or 603 corresponds to the determined size of the simulated iris 601 or 603, then the microprocessor circuit 205 may determine that no change to the current size of the simulated iris 601 or 603 is necessary. Accordingly, the microprocessor circuit 205 may allow the simulated iris 601 or 603 to remain in its reported current size. However, if, based on the comparison of the current size and the determined size of the simulated iris 601 or 603, the microprocessor circuit 205 determines that the current size does not correspond to the determined size of the simulated iris 601 or 603, then the microprocessor circuit 205 determines that the size of the simulated iris 601 or 603 should be changed to the determined size.

The microprocessor circuit 205 may then operate the iris motor 244 or 249 of the corresponding eye to effect the constriction or the dilation of the simulated iris 601 or 603 of the eye. Once the size of the simulated iris 601 or 603 has been changed to the determined size, the microprocessor circuit 205 may determine that the other eye that is not directly simulated by the specific light conditions may also need to be constricted or dilated in response to the specific light conditions discussed herein. The microprocessor circuit 205 may effect constriction or dilation of the simulated iris 601 or 603 in the other eye by following similar steps as discussed herein for the given eye that is directly simulated by the specific light conditions. Further, the microprocessor circuit 205 may effect constriction or dilation of the simulated iris 601 or 603 in the other eye by a different amount with respect to the given eye. Once the sizes of both the simulated irises 601 or 603 have been changed to the determined sizes of the simulated irises 601 or 603, the above procedure may be repeated so that the patient simulator 200 realistically replicates the change in size of an iris in a human eye in a way that is useful for medical educational and diagnostic purposes. When the pupillary change functionality is stopped, the microprocessor circuit 205 places both the simulated irises 601 and 603 in their default sizes to simulate normal lighting conditions.

Figure 6:
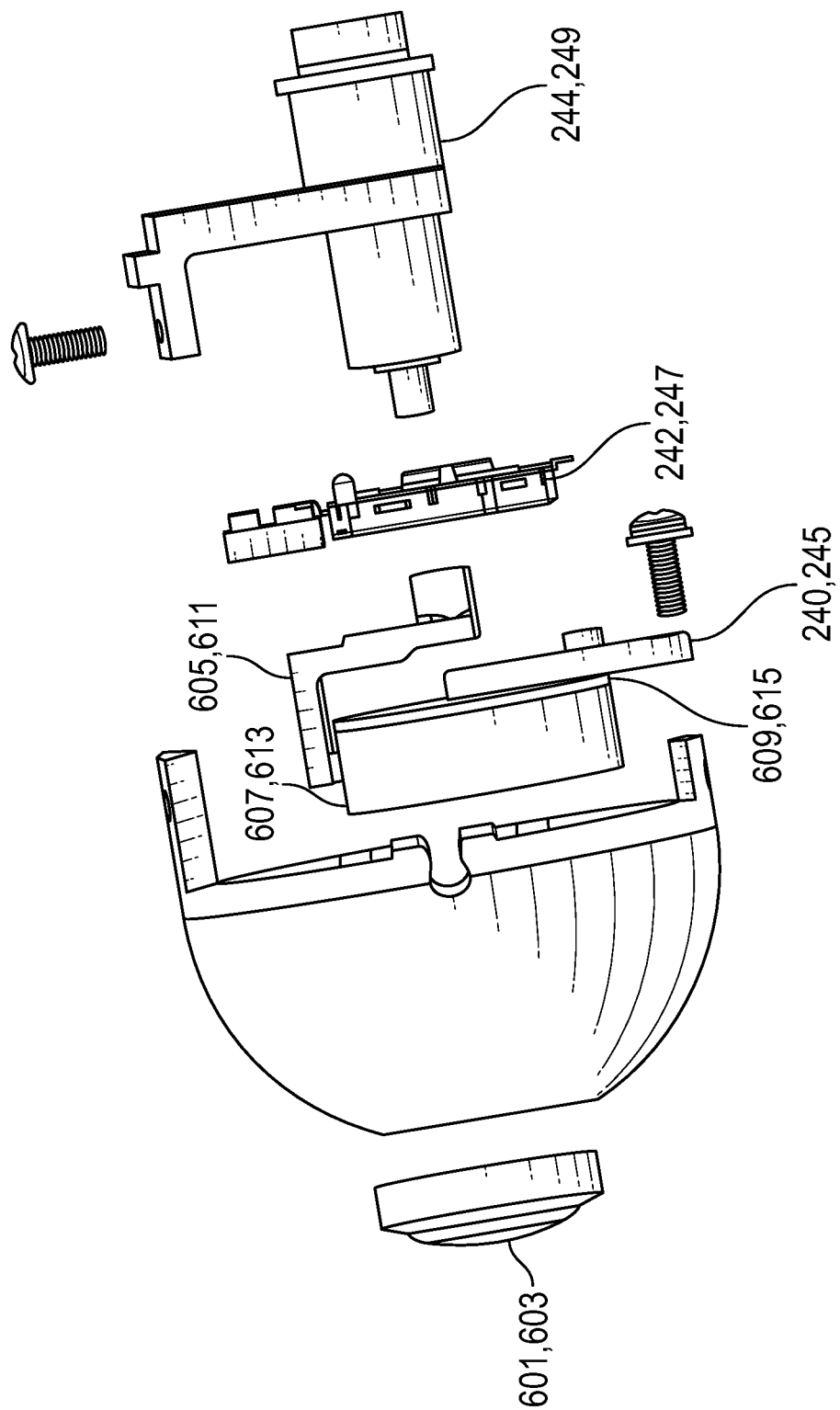
FIG. 6 is an exploded view of the left or right eye assembly of FIGS. 3 and 4, according to various embodiments of the present disclosure.

Turning also to FIG. 6, with continuing reference to FIGS. 1 and 2, in various embodiments, the iris motor may be a geared motor coupled to a rotating arm that enables the circular aperture of the eye to circularly reduce in size when simulating constriction and to circularly increase in size when simulating dilation. In various embodiments the circular aperture may constrict to a circular size of about 1 mm in diameter and may dilate to a circular size of about 8 mm in diameter. That is, the circular aperture may have a circular size between 1 mm in diameter to 8 mm in diameter. In its default position, which may simulate normal light conditions, the circular aperture may have a circular size of about 4 mm in diameter. Also, the circular aperture may be of a blue or brown color to simulate a blue or brown iris in the eye. The circular aperture is attached to the background that simulates a pupil of a human eye. As the circular size of the aperture is changed with the background simulating the pupil, realistic replication of an iris (of a human eye) changing circular size in response to the surrounding lighting conditions is achieved.

More particularly, the left and right iris motors 244 and 249 are respectively connected to the left and right iris size sensors 242 and 247 via left and right rotating arms 605 and 611. The left and right rotating arms 605 and 611 are respectively connected to left and right circular apertures 607 and 613, which represent the left and right simulated irises 601 and 603 in the respective left and right eye assemblies 101 and 105. The left and right apertures 607 and 613 are adjacently placed next to left and right pupil backgrounds 609 and 615, respectively. In various embodiments, the electro-mechanical components operable to effect pupillary changes are coupled to each other coaxially. The above-described components for actuating the constriction or dilation of the left and right apertures 607 and 613 are placed inside the respective left and right eye assemblies 101 and 105—this allows the control associated with the constriction or dilation of the simulated left and right irises 601 and 603 to be independent from the horizontal or vertical movements of the simulated left and right pupils 106 and 107 discussed herein in connection with FIGS. 3-5.

The respective shafts of the left and right iris motors 244 and 249 may be coupled to the left and right rotating arms 605 and 611 such that rotation of the motors effects rotation of the rotating arms. Further, the respective left and right rotating arms 605 and 611 may be coupled to the circular apertures 607 and 613 that act as the simulated left and right irises 601 and 603 such that rotation of the rotating arms allows for increase or decrease in the size of the circular apertures. For example, when an iris motor (244 or 249) rotates in a first direction, it effects rotation of the associated rotating arm (601 or 607) to increase the circular size of the circular aperture (603 or 609). Similarly, when the iris motor (244 or 249) rotates in a second direction, it effects rotation of the associated rotating arm (601 or 603) to decrease the circular size of the circular aperture (603 or 609). The increase or decrease in the size of the circular apertures 607 and 613 along with the pupil backgrounds 609 and 615 visually simulates constriction or dilation of an iris in a human eye.

The total range of change in the size of the iris may be from 1 mm in diameter when totally constricted to 8 mm in diameter when totally dilated. The total range may include three illustrated positions—a default size, a totally constricted size, and a totally dilated size. In various embodiments, the default size of the iris may be about 4 mm in diameter, the totally constricted size of the iris may be about 1 mm in diameter, and the totally dilated size of the iris may be about 8 mm in diameter.

Blinking Movement:

Blinking may be described as a physiological response which involves the closing and opening of an eyelid of an eye. Blinking is a normal reflex and protects the eyes from dryness, and also regulates tear production to nourish and cleanse the surface of the eye. The blinking rate, which is the rate at which an eyelid closes and opens per unit of time, is an important medical indicator for healthy eyes. For example, healthy eyes exhibit a low rate of blinking of about 5-10 blinks per minute. On the other hand, an excessive blinking rate of about 30 blinks per minute and higher indicates unhealthy conditions such as dry eyes, nervousness, eye irritation, or psychiatric conditions. In various embodiments, the presently disclosed simulator realistically replicates the blinking of a human eye in a way that is useful for medical educational and diagnostic purposes.

Referring back again to FIG. 2, in various embodiments, the patient simulator 200 is configured to simulate blinking of human eyes—for example, the simulate left and right simulated eyelids 108 and 109 are operated to open and close to simulate blinking. In various embodiments, the rate, pattern, and speed of blinking are controlled by the microprocessor circuit 205 illustrated in FIG. 2. In some instances, the rate of blinking ranges from 5 blinks per minute to 30 blinks per minute. However, ranges outside of this are used in some embodiments. Further, the eyes can be maintained in an open position or a closed position. The speed of the blinks can be controlled as well. In some instances, the speed of each blink from an open position to a closed position and back to the open position is approximately 200 ms. However, the speed of the blinks can be increased or decreased as desired.

As discussed herein, the left eye assembly 101 includes the left eyelid 108 along with associated circuitry to control functions to be performed by the left eye assembly 101, and the right eye assembly 105 includes the right eyelid 109 along with associated circuitry to control functions to be performed by the right eye assembly 105. In various embodiments, the left and right simulated eyelids 108 and 109 are moved together to simulate blinking.

To simulate the realistic blinking features discussed herein, the patient simulator 200 may include the microprocessor circuit 205 electrically connected to an eyelid position sensor 250 and a blink motor 252 to actuate the left and right simulated eyelids 108 and 109 to simulate blinking. In various embodiments, the blinking of the left and right simulated eyelids 108 and 109 may be controlled independently, and each eyelids may have a dedicated blink motor to actuate the independently simulate blinking. The blinking may involve the left and right simulated eyelids 108 and 109 moving between an open position and a closed position, with the open position being the default position of the left and right simulated eyelids 108 and 109.

Figure 7:
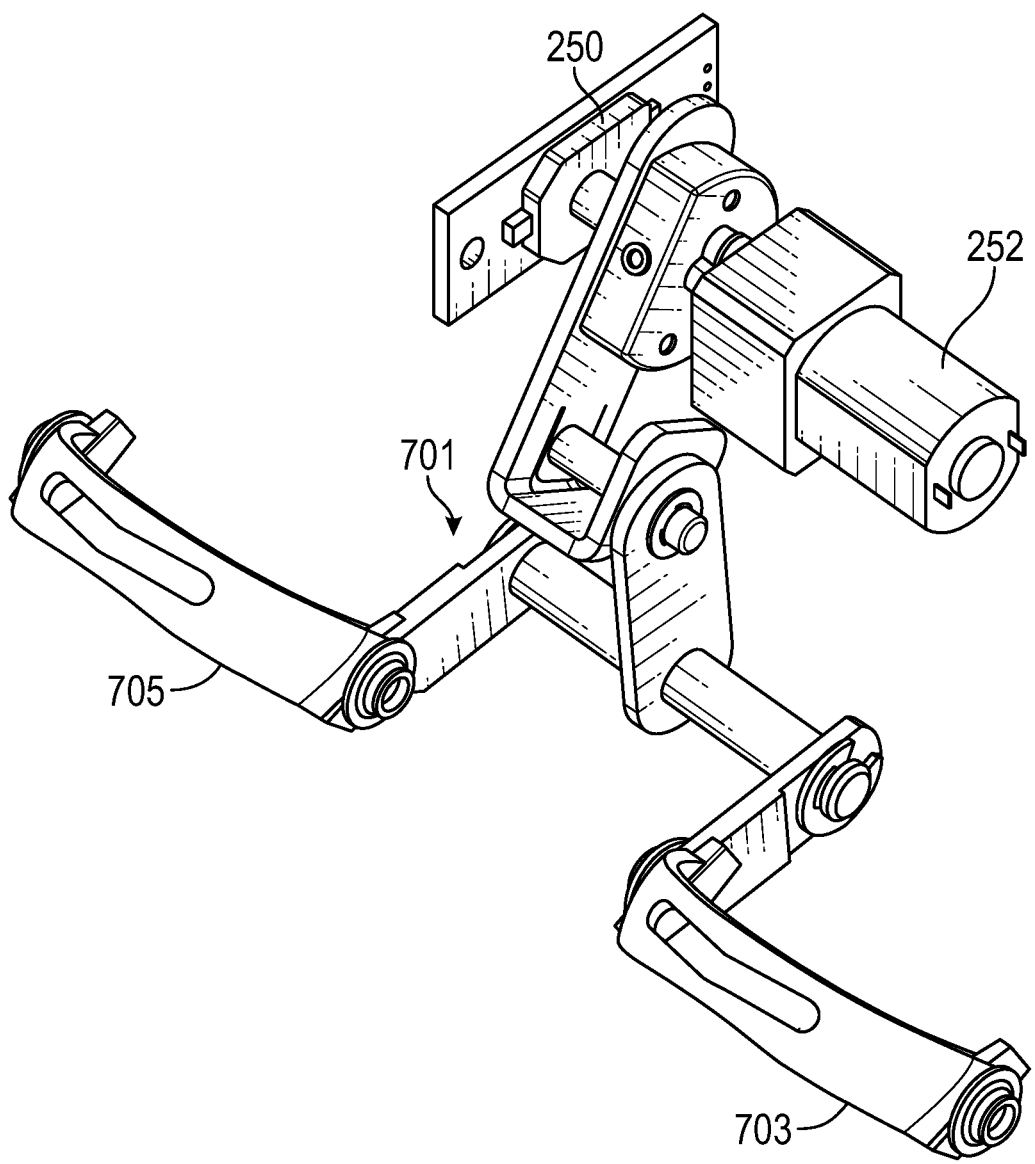
FIG. 7 is a perspective view of an apparatus for effecting vertical movement of simulated left and right eyelids, which may be implemented at least in part within the manikin, the patient simulator, and/or the respective environments of FIGS. 1 and 2, according to various embodiments of the present disclosure.

Turning also to FIG. 7, with continuing reference to FIGS. 1 and 2, in various embodiments, the blink motor 252 is attached to a linkage 701 (e.g., a four-bar linkage) capable of relaying the torque of the blink motor 252 to a pair of rotatable curved parts 703 and 705. The rotatable curved parts 703 and 705 may be covered by silicone material serving as the respective left and right simulated eyelids 108 and 109. Accordingly, when the microprocessor circuit 205 operates the blink motor 252 to rotate, the linkage 701 relays the torque to the two rotatable curved parts 703 and 705 (i.e., the left and right simulated eyelids 108 and 109) to simulate human blinking motion.

The microprocessor circuit 205 may instruct the eyelid position sensor 250 to report the current position of the two rotatable curved parts 703 and 705 (i.e., the left and right simulated eyelids 108 and 109). Further, the microprocessor circuit 205 may continuously receive electrical signals from the eyelid position sensor 250 to continuously monitor positions of the left and right simulated eyelids 108 and 109. In various embodiments, the microprocessor circuit 205 may continuously monitor the positions of the left and right simulated eyelids 108 and 109 when the blinking is actuated between the open and closed positions. During the monitoring, when the microprocessor circuit 205 determines that the left and right simulated eyelids 108 and 109 have reached the closed position, the microprocessor circuit 205 may emit electrical signals to reverse the rotation of the blink motor 252 so that the left and right simulated eyelids 108 and 109 are rotated to the open position.

In various embodiments, the sensors 230, 232, 235, 237, 242, 247, and 250 discussed herein with respect to sensing the respective positions of the pupils 106 and 107, the respective sizes of the simulated irises 601 and 603, and the position (or respective positions) of the simulated eyelids 108 and 109 may be rotary potentiometers. The rotary potentiometers may be electro-mechanically connected to the microprocessor circuit 205 and to shafts of the respective associated motors discussed herein. The rotary potentiometers may be used as both the dividers to obtain adjustable output voltages. As a motor shaft rotates, the wiper (i.e., the sliding contact) of the corresponding rotary potentiometer slides along the resistive body between the terminals of the potentiometer. The sliding of the wiper provides a reading of the adjustable output voltage.

The microprocessor circuit 205 monitors the adjustable output voltage, and refers to respective predetermined associations between output voltages and the positions of the simulated pupils 106 and 107, the sizes of the simulated irises 601 and 603, or the positions of the simulated eyelids 108 and 109 to determine respective current positions. For example, the microprocessor circuit 205 may monitor the adjustable output voltage output by the left pupil position sensor 230, and refer to a predetermined association between the output voltage of the left pupil position sensor 230 and the position of the simulated left pupil 106 to determine a current position of the simulated left pupil 106. Similarly, the microprocessor circuit 205 may monitor the adjustable output voltage output by the eyelid position sensor 250, and refer to a predetermined association between the output voltages of the eyelid position sensor 250 and the position(s) of the simulated eyelids 108 and 109 to determine current positions of the simulated eyelids 108 and 109. Finally, the microprocessor circuit 205 may monitor the adjustable output voltage output by the left iris size sensor 242, and refer to a predetermined association between the output voltages of the left iris size sensor 242 and the size of the simulated left iris 601 to determine a current size of the simulated left iris 601. In addition to determining current positions and sizes, as discussed herein, the microprocessor circuit 205 may also use the monitored adjustable output voltages to confirm that the effected changes in the positions of the pupils and/or the eyelids and in the sizes of the irises have been accurately effected.

In human eyes, the simulated left and right eyelids 108 and 109 should also move upward and downward along with the upward and downward movement of the simulated left and right pupils 106 and 107—this is called eyelid following. It is critical that medical simulators test and diagnose this phenomenon. The present simulator mimics the lifelike motion of the eyelids during eyelid following. More particularly, the motion of the simulated left and right eyelids 108 and 109 relates to the vertical motion of the simulated left and right pupils 106 and 107. As the simulated left and right pupils 106 and 107 move upward or downward, the simulated left and right eyelids 108 and 109 follow the simulated left and right pupils 106 and 107 to maintain a constant distance between the pupils and the eyelids. For example, when the simulated left pupil 106 moves downward, the simulated left eyelid 108 follows the simulated left pupil 106 to maintain a constant distance between the simulated left pupil 106 and the simulated left eyelid 108. In this case, the simulated left eyelid 108 moves downward towards its closed position but remains open enough to maintain the constant distance. Similarly, when the simulated right pupil 107 moves upward, the simulated right eyelid 109 follows the simulated right pupil 107 to maintain a constant distance between the simulated right pupil 107 and the simulated right eyelid 109. In this case, the simulated right eyelid 109 moves upwards past its open position to maintain the constant distance. When the simulated left and right pupils 106 and 107 are looking substantially straight, the simulated left and right eyelids 108 and 109 are positioned in their nominal open positions. The patient simulator may employ the same assemblies as employed for the eyelid blinking and vertical motion of the pupils discussed herein. The simulated left and right pupils 106 and 107 act as the master since the simulated left and right eyelids 108 and 109 react to the movement of the simulated left and right pupils 106 and 107.

Tear Duct Activation:

Referring back again to FIG. 2, in various embodiments, to activate the tear duct assembly 110, the patient simulator 200 may include the microprocessor circuit 205 electrically connected to a left pump 255 and a right pump 257. In various embodiments, the left and right pumps 255 and 257 are peristaltic pumps. The separate left and right pumps 255 and 257 allow independent control of tear production by the tear duct assembly 110 for the left and right sides of the manikin 100. The independent control of tear production for the left and right sides of the manikin 100 is relevant because it may contribute to the simulated expression of a clinical response (e.g., pain) by the manikin 100—realistic tear production is critical in the face for accurately expressing pain and emotion. More particularly, to simulate the realistic tear production discussed herein, the microprocessor circuit 205 determines a desired clinical response (e.g., pain) to be simulated by the manikin 100—in various embodiments, the desired clinical response is determined based on one or more user inputs, a predetermined medical training scenario, one or more artificial or sensed external conditions, or any combination thereof.

Once the microprocessor circuit 205 has determined the desired clinical response for a given medical training exercise, the microprocessor circuit 205 may determine the current state of the left and right pumps 255 and 257 (e.g., on, off, flow rate, stroke rate, revolution rate, and/or the like). The microprocessor circuit 205 may then independently compare the current states of the left and right pumps 255 and 257 with respect to the desired clinical response, and determine whether the current states of the left and right pumps 255 and 257 correspond to the desired clinical response. The microprocessor circuit 205 may determine to effect no change in the current states of the left and right pumps 255 and 257 when it is determined that the current state of the tear duct assembly 110 corresponds to the desired clinical response. However, the microprocessor circuit 205 may instruct the left pump 255 to change the current state of the left pump 255 when it is determined that the current state of the left pump 255 does not correspond to the desired clinical response. For example, the microprocessor circuit 205 may instruct the left pump 255 to change its state such that a fluid pumped by the left pump 255 flows in accordance with the desired clinical response. Similarly, the microprocessor circuit 205 may instruct the right pump 257 to change the current state of the right pump 257 when it is determined that the current state of the right pump 257 does not correspond to the desired clinical response. For example, the microprocessor circuit 205 may instruct the right pump 257 to change its state such that a fluid pumped by the right pump 257 flows in accordance with the desired clinical response.

In various embodiments, the microprocessor circuit 205 may change the respective states of the left and right pumps 255 and 257—the ability of the patient simulator 200 to effect changes in the states of the left and right pumps 255 and 257 allows the patient simulator to realistically simulate various clinical and/or emotional responses (e.g., pain, sadness, stroke symptoms, etc.) using the manikin 100. Further, the microprocessor circuit 205 may change the current state of the left pump 255 independently from the current state of the right pump 257. Further, the microprocessor circuit 205 may change the current state of the left pump 255 by an amount of displacement that is lower than, equal to, or greater than an amount of displacement of the right pump 257, and vice versa.

Figure 8:
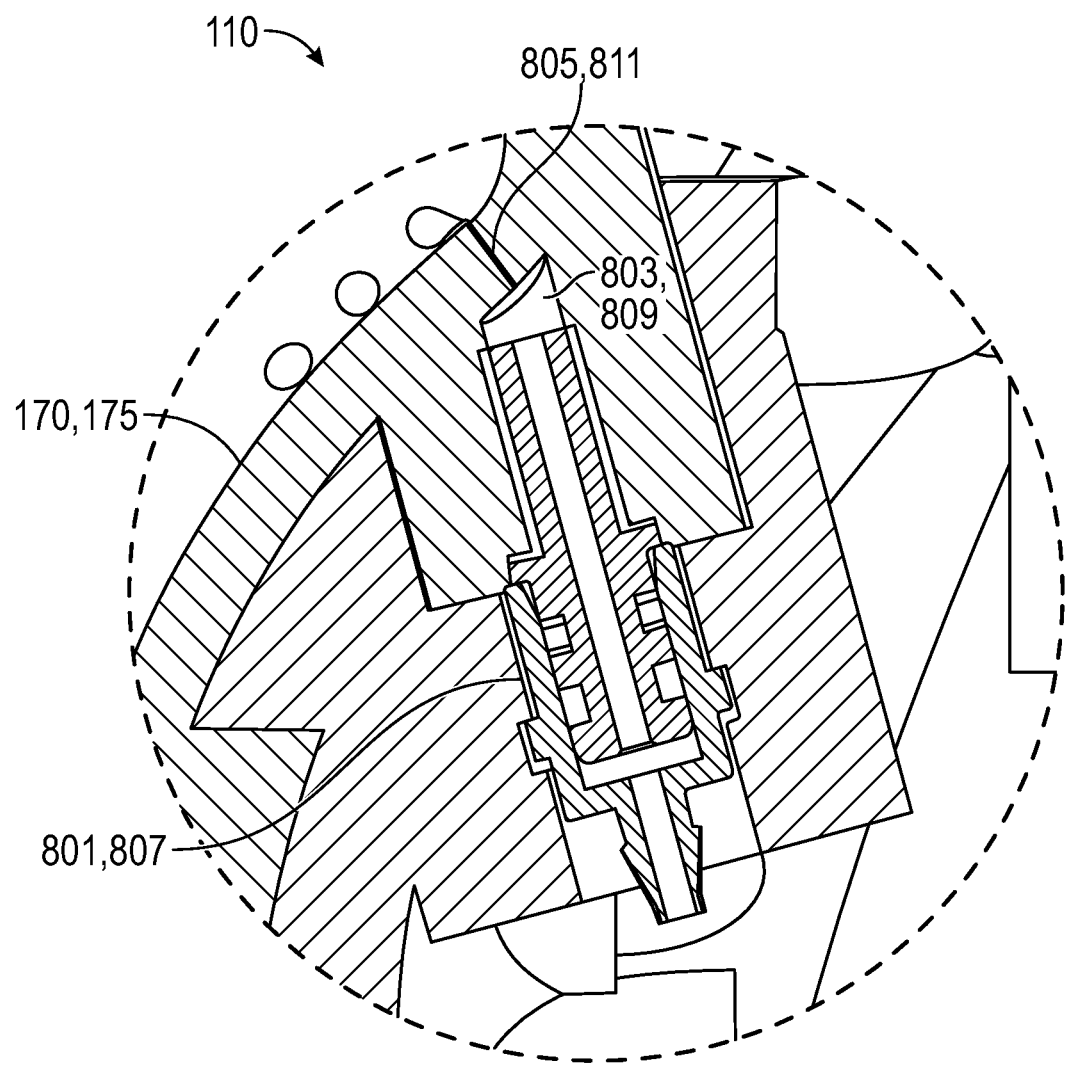
FIG. 8 is a cross sectional view of at least part of a tear duct assembly, which may be implemented at least in part within the manikin, the patient simulator, and/or the respective environments of FIGS. 1 and 2, according to various embodiments of the present disclosure.
Figure 9:
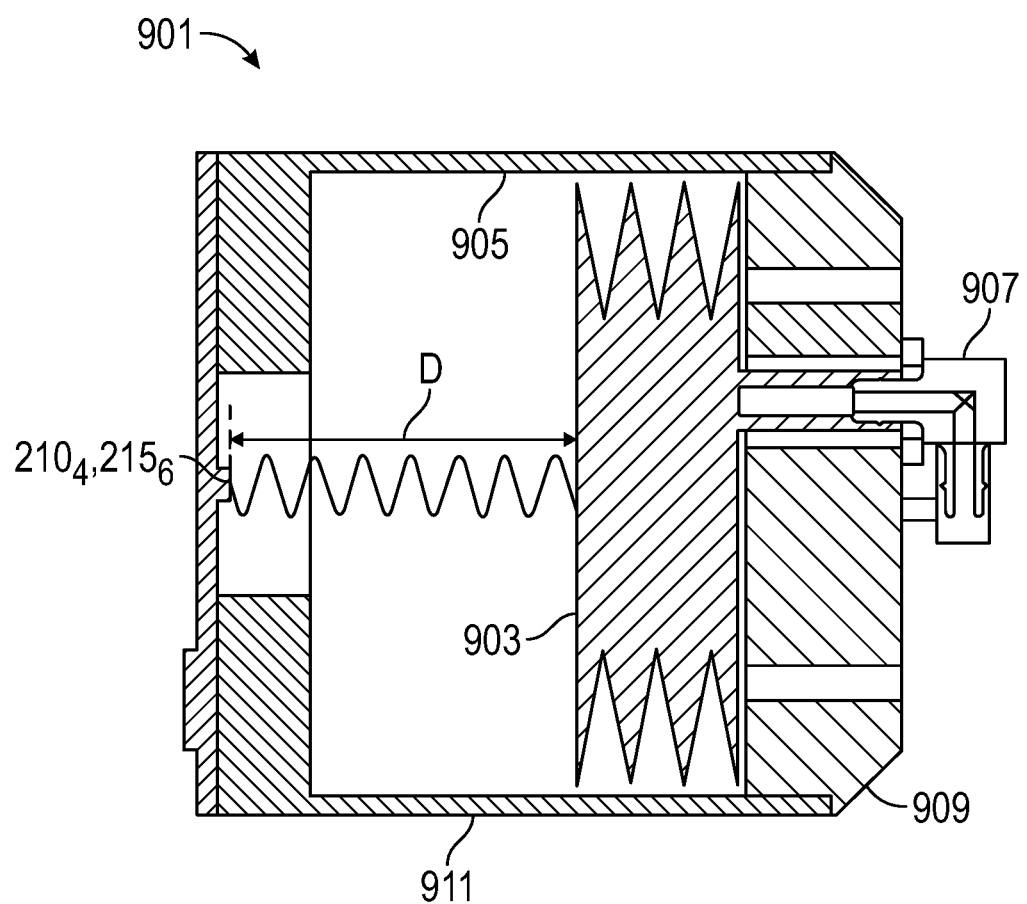
FIG. 9 is a cross sectional view of a fluid reservoir that communicates fluidically with the at least part of the tear duct assembly illustrated in FIG. 8, according to various embodiments of the present disclosure.

Turning also to FIGS. 8 and 9, with continuing reference to FIGS. 1 and 2, in various embodiments, the left and right pumps 255 and 257 are in fluid communication with left and right tear fittings 801 and 807 of the tear duct assembly 110. As shown in FIG. 8, the left and right tear fittings 801 and 807 may be covered by silicone material serving as simulated left and right cheeks 170 and 175 of the manikin 100. The left and right tear fittings 801 and 807 communicate with fluid chambers 803 and 809 formed in the respective interiors of the left and right simulated cheeks 170 and 175. The simulated left and right cheeks 170 and 175 include artificial pores 805 and 811 extending from the fluid chambers 803 and 809 to respective exteriors of the simulated left and right cheeks 170 and 175. To realistically simulate the appearance of human tear ducts, a thin needle (~0.05 inch diameter) is passed through the silicone skin to form the artificial pores 805 and 807—the silicone skin is not cored by the needle because the needle is so thin. The needle forms a small aperture through the silicone skin so that, once the needle is removed, the silicone skin collapses back on itself to hide the aperture. As a result, realistic tear production is simulated when the microprocessor circuit 205 operates the left and right pumps 255 and 257 to communicate fluid to the respective left and right tear fittings 801 and 807, which fluid flows into the fluid chambers 803 and 809, through the artificial pores 805 and 811, and onto respective exteriors of the simulated left and right cheeks 170 and 175, as shown in FIG. 8. The fluid forms tear-like beads on the respective exteriors of the simulated left and right cheeks 170 and 175—each bead grows in size until it is large enough to roll down the simulated left or right cheek 170 or 175.

As shown in FIG. 9, in various embodiments, the tear duct assembly 110 further includes a fluid reservoir 901 from which the left and right pumps 255 and 257 draw fluid to communicate to the respective left and right tear fittings 801 and 807. Detecting the fluid level within the fluid reservoir 901 can be challenging due to the potentially changing nature of the patient simulator 200's orientation (which may be implemented at least in part within the environment and/or the manikin 100). To address this issue, the fluid reservoir 901 includes an expandable vessel 903 (e.g., an accordion- or bellows-type bag) enclosed within an expansion chamber 905. The expandable vessel 903 is configured to be actuable between a fully-collapsed state to a fully-expanded state within the expansion chamber 905. The expandable vessel 903 may be filled or emptied via a port 907 connected thereto—in various embodiments, the port 907 communicates fluidically with both a filling line (not shown) and the left and right pumps 255 and 257.

As the expandable vessel 903 is filled with fluid via the filling line and the port 907), the expandable vessel 903 expands towards the fully-expanded state—such expansion causes the expandable vessel 903 to lengthen within the expansion chamber 905. The expansion and lengthening of the expandable vessel 903 causes it to apply a reaction force to the fluid contained therein. Once fully expanded or lengthened, the expandable vessel 903 is in its highest energy state. On the other hand, the expandable vessel 903 contracts towards the fully-collapsed state as fluid is emptied therefrom via the port 907—such contraction causes the expandable vessel 903 to shorten within the expansion chamber 905, thereby decreasing the reaction force applied to the fluid. Once fully contracted or shortened, the expandable vessel 903 is in its lowest energy state and applies zero or very little reaction force to any remaining fluid contained therein. The total length of the expandable vessel 903 within the expansion chamber 905 is therefore a function of the amount of fluid contained within the expandable vessel at any given time—gravity has only a negligible effect because the magnitude of the expandable vessel 903's reaction force is significantly greater than the force of gravity.

The expandable vessel 903 is fixed to a housing 909 that defines the expansion chamber 905 so that lengthening of the expandable vessel 903 within the expansion chamber 905 occurs in a single direction. The housing 909 includes sidewall(s) 911 to prevent "leaning" of the expandable vessel 903 within the expansion chamber 905 as the expandable vessel 903 lengthens and shortens. The amount of lengthening or shortening of the expandable vessel 903 within the expansion chamber 905 is directly correlated to the amount of fluid contained within the expandable vessel 903 at any given time. To measure the amount of lengthening or shortening of the expandable vessel 903 within the expansion chamber 905, and thus the amount of fluid contained within the expandable vessel 903, at least one of the IR sensors $210_{1-N}$ (e.g., the IR sensor $210_4$) and at least one of the IR emitters $215_{1-N}$ (e.g., the IR emitter $215_6$) is positioned at or near the expansion chamber 905. This sensor/emitter pair (i.e., the IR sensor $210_4$ and the IR emitter $215_6$) is capable of measuring a distance D indicative of the lengthening or shortening of the expandable vessel 903. In various embodiments, one or more parts of the housing 909, including at least the sidewall(s) 911, are made of a material having a higher IR absorptivity than that of the expandable vessel 903 so as to minimize measurement errors.

More particularly, the IR emitter $215_6$ emits pulses of IR light that reflect off of the expandable vessel 903. The magnitude of the reflected IR light is then measured by the IR sensor $210_4$. The amount of IR light reflected is a function of the distance D between the IR sensor $210_4$ and the expandable vessel 903—closer objects reflect more IR light and distant object reflect less IR light. Accordingly, the amount of IR light reflected increases as the expandable vessel 903 fills with fluid and lengthens towards the IR sensor $210_4$, and the amount of IR light reflected decreases as the expandable vessel 903 is emptied and shortens away from the IR sensor $210_4$. However, the relationship between the amount of fluid in the expandable vessel 903 and the amount of IR light reflected is not linear, but is instead most closely matched with a polynomial—the microprocessor circuit 205 employs this polynomial to convert the measurements of reflected IR light to a volume of fluid within the expandable vessel 903.

Brow Movement:

Referring back again to FIG. 2, in various embodiments, to impart vertical (up and down) movement to the simulated left brow 117 and the simulated right brow 118, the patient simulator 200 may include the microprocessor circuit 205 electrically connected to a left brow position sensor 260, a left brow motor 261, a right brow position sensor 262, and a right brow motor 263. In various embodiments, the left and right brow motors 261 and 263 are DC gear motors, and the left and right brow position sensors 260 and 262 are resistive absolute position sensors. The separate left and right brow motors 261 and 263 allow independent control of vertical (up and down) movement of the simulated left brow 117 and the simulated right brow 118, respectively. The independent vertical control of the simulated left brow 117 and the simulated right brow 118 is relevant because it allows medical tests to be performed individually on each brow, and may contribute to the simulated expression of a clinical response (e.g., pain) by the manikin 100—realistic brow motion is critical in the face for accurately expressing pain and emotion. The left and right brow position sensors 260 and 262 may be rotary position sensors that sense rotational positions of the simulated left and right brows 117 and 118, respectively.

More particularly, to simulate the realistic brow movement features discussed herein, the microprocessor circuit 205 determines a desired clinical response (e.g., pain) to be simulated by the manikin 100—in various embodiments, the desired clinical response is determined based on one or more user inputs, a predetermined medical training scenario, one or more artificial or sensed external conditions, or any combination thereof. Once the microprocessor circuit 205 has determined the desired clinical response for a given medical training exercise, the microprocessor circuit 205 may instruct the left brow position sensor 260 to report a current position of the simulated left brow 117, and may instruct the right brow position sensor 262 to report a current position of the simulated right brow 118. The microprocessor circuit 205 may then independently compare the current positions of the simulated left and right brows 117 and 118 with respect to the desired clinical response, and determine whether the current positions of the simulated left and right brows 117 and 118 correspond to the desired clinical response. For example, to determine whether the current positions of the simulated left and right brows 117 and 118 correspond to the desired clinical response, the microprocessor circuit 205 may determine whether the current positions of the simulated left and right brows 117 and 118 are oriented in accordance with the desired clinical response.

The microprocessor circuit 205 may determine to effect no change in the current positions of the simulated left and right brows 117 and 118 when it is determined that the current positions of both the simulated left and right brows 117 and 118 correspond to the desired clinical response. However, the microprocessor circuit 205 may instruct the left brow motor 261 to change the current position of the simulated left brow 117 when it is determined that the current position of the simulated left brow 117 does not correspond to the desired clinical response. For example, the microprocessor circuit 205 may instruct the left brow motor 261 to position the simulated left brow 117 such that the simulated left brow 117 is oriented in accordance with the desired clinical response. Similarly, the microprocessor circuit 205 may instruct the right brow motor 263 to change the current position of the simulated right brow 118 when it is determined that the current position of the simulated right brow 118 does not correspond to the desired clinical response. For example, the microprocessor circuit 205 may instruct the right brow motor 263 to position the simulated right brow 118 such that the simulated right brow 118 is oriented in accordance with the desired clinical response.

In various embodiments, the microprocessor circuit 205 may change the positions of the simulated left and right brows 117 and 118 in the vertical (up and down) direction. The ability of the patient simulator 200 to effect changes in the positions of the simulated left and right brows 117 and 118 in the vertical (up and down) direction allows the patient simulator to realistically simulate various medical tests performed by doctors on human brows, and contributes at least partially to the expression of the desired clinical response (e.g., pain) by the manikin 100. Further, the microprocessor circuit 205 may change the current position of the simulated left brow 117 independently from the current position of the simulated right brow 118. Further, the microprocessor circuit 205 may change the current position of the simulated left brow 117 by an amount of displacement that is lower than, equal to, or greater than an amount of displacement of the simulated right brow 118, and vice versa.

Figure 10:
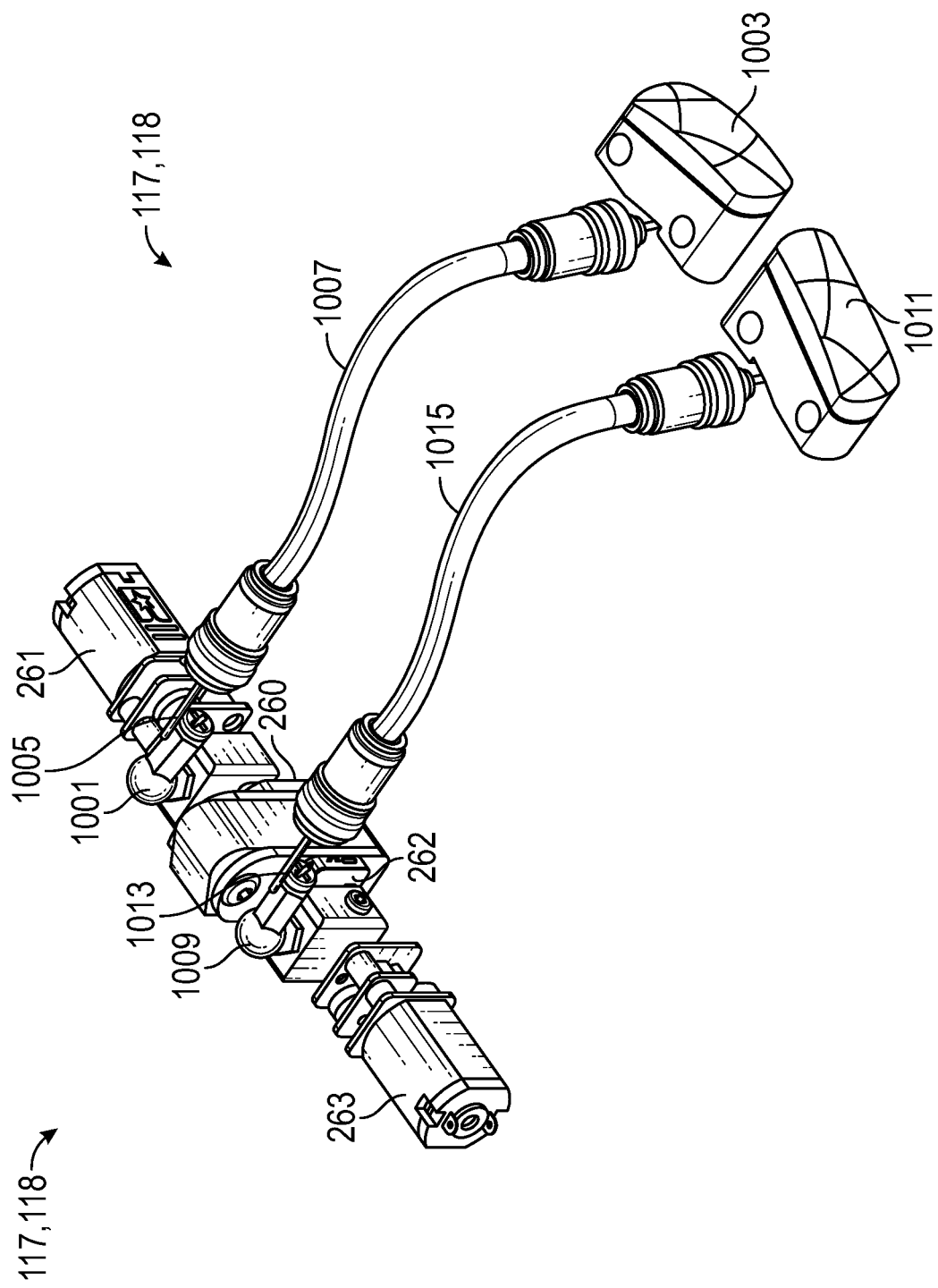
FIG. 10 is a perspective view of a brow assembly, which may be implemented at least in part within the manikin, the patient simulator, and/or the respective environments of FIGS. 1 and 2, according to various embodiments of the present disclosure.

Turning also to FIG. 10, with continuing reference to FIGS. 1 and 2, in various embodiments, the left and right brow motors 261 and 263 are attached to left and right motor arms 1001 and 1009 capable of relaying torque from the left and right brow motors 261 and 263 to left and right brow hard points 1003 and 1011, respectively. More particularly, the left and right motor arms 1001 and 1009 are attached to thin flexible rods 1005 and 1013—the respective rods 1005 and 1013 form part of left and right Bowden cables 1007 and 1015 connecting the left and right motor arms 1001 and 1009 to the left and right brow hard points 1003 and 1011. Due to limited space near the front of the manikin 100, the left and right Bowden cables 1007 and 1015 are needed to emit force from the distant left and right brow motors 261 and 263 to the left and right brow hard points 1003 and 1011, respectively, in the face of the manikin 100. The left and right brow hard points 1003 and 1011 may be covered by silicone material serving as the simulated left and right brows 117 and 118. Accordingly, when the microprocessor circuit 205 operates the left and right brow motors 261 and 263 to rotate, the left and right motor arms 1001 and 1009, along with the left and right Bowden cables 1007 and 1015, relay the torque to the left and right brow hard points 1003 and 1011 (i.e., the left and right simulated brows 117 and 118) to simulate, for example, the furrowing or raising motion of a human brow. In various embodiments, the simulated left and right brows 117 and 118 can also be manually moved by the user.

The left and right brow position sensors 260 and 262 are attached to the motor shafts of the left and right brow motors 261 and 263. Accordingly, the microprocessor circuit 205 may instruct the left and right brow position sensors 260 and 262 to report the current positions of the left and right brow hard points 1003 and 10013 (i.e., the left and right simulated brows 117 and 118). Further, the microprocessor circuit 205 may continuously receive electrical signals from the left and right brow position sensors 260 and 262 to continuously monitor positions of the left and right simulated brows 117 and 118. In various embodiments, the microprocessor circuit 205 may continuously monitor the positions of the left and right simulated brows 117 and 118 when the left and right brow hard points 1003 and 1011 are actuated between the furrowed and raised positions. During the monitoring, when the microprocessor circuit 205 determines that the left and right simulated brows 117 and 118 have reached the desired position, the microprocessor circuit 205 may emit electrical signals to maintain the respective positions of the left and right brow motors 261 and 263 so that the left and right simulated brows 117 and 118 are held in position.

In various embodiments, the sensors 260 and 262 discussed herein with respect to sensing the respective positions of the brows 117 and 118 may be rotary potentiometers. The rotary potentiometers may be electromechanically connected to the microprocessor circuit 205 and to shafts of the respective associated motors discussed herein. The rotary potentiometers may be used as both the dividers to obtain adjustable output voltages. As a motor shaft rotates, the wiper (i.e., the sliding contact) of the corresponding rotary potentiometer slides along the resistive body between the terminals of the potentiometer. The sliding of the wiper provides a reading of the adjustable output voltage. The microprocessor circuit 205 monitors the adjustable output voltage, and refers to respective predetermined associations between output voltages and the positions of the simulated brows 117 and 118 to determine respective current positions. For example, the microprocessor circuit 205 may monitor the adjustable output voltage output by the left brow position sensor 260 and refer to a predetermined association between the output voltage of the left brow position sensor 260 and the position of the simulated left brow 117 to determine a current position of the simulated left brow 117. In addition to determining current positions, as discussed herein, the microprocessor circuit 205 may also use the monitored adjustable output voltages to confirm that the effected changes in the positions of the brows have been accurately effected.

Neck Movement:

Referring back again to FIG. 2, in various embodiments, to impart horizontal (left and right) movement to the simulated neck 122, the patient simulator 200 includes a neck position sensor 265 and a neck motor 267. In various embodiments, the neck motor 267 is a DC gear motor and the neck position sensor is a resistive absolute position sensor. The horizontal control of the simulated neck 122 is relevant because it allows medical tests to be performed on the simulated neck (e.g., impaired neck movement may indicate that the patient has suffered from or is at risk of suffering from torticollis). The neck position sensor 265 may be a rotary position sensor that senses rotational positions of the simulated neck 122. To simulate the neck movement and neck tracking features discussed herein, the microprocessor circuit 205 instructs at least one of the IR emitters $215_{1-N}$ (i.e., the IR emitters $215_{1-2}$) to emit IR radiation and instructs at least one of the IR sensors $210_{1-N}$ (e.g., the IR sensors $210_{1-3}$) to sense the IR response signals reflected off of an approaching or passing object. However, if the patient simulator 200 is set to have an impairment with respect to the simulated neck 122, such as, for example, torticollis, the neck tracking features discussed herein can be disabled. The manner in which the microprocessor circuit 205 determines the presence and location of the approaching or passing object in order to simulate the neck movement and neck tracking features is substantially similar to that discussed herein with respect to the eye movement and eye tracking features.

More particularly, in various embodiments, the neck assembly 120 uses at least two (2) of the IR emitters $215_{1-2}$ and at least two (2) of the IR sensors $210_{1-3}$—one or more of the IR sensors may also be used for the eye tracking features discussed herein. Accordingly, the IR sensors $210_{1-3}$ may be multiplexed in time between the various IR emitters $215_{1-5}$ used for the eye and neck tracking features discussed herein. In operation, the left IR emitter $215_2$ emits a short burst of IR light, which radiates from the manikin 100 and reflects off of any objects within, for example, about 3 feet. At least the left IR sensor $210_3$ measures the amount of IR light reflected off of the object and, if the amount of reflected IR light is large enough, the microprocessor circuit 205 will recognize that there is a human-sized body approaching or passing on the left side of the manikin 100. However, if the amount of reflected IR light is low, the microprocessor circuit 205 will recognize that there is not a human-sized body approaching or passing on the left side of the manikin 100. The right IR emitter $215_1$ and at least the right IR sensor $210_1$ operate similarly to detect objects on the right side of the manikin 100. The outcome of these readings affects the movement of the neck assembly 120, but does not affect the eye tracking features discussed herein. The neck tracking operates continuously to detect changes to react to in the environment surrounding the manikin 100.

In various embodiments, to prevent interference, only one sensor/emitter pair is active at any given time. For example, the following sensor/emitter pairs may be activated in a sequential loop (in any order) to facilitate the neck tracking and eye tracking features discussed herein: the IR sensor $210_3$ is paired with the IR emitter $215_2$ for neck tracking to detect objects on the left side of the manikin 100; the IR sensor $210_1$ is paired with the IR emitter $215_1$ for neck tracking to detect objects on the right side of the manikin 100; the IR sensor $210_3$ is paired with the IR emitter $215_5$ for eye tracking to detect objects on the left side of the manikin 100; the IR sensor $210_2$ is paired with the IR emitter $215_4$ for eye tracking to detect objects directly in front of the manikin 100; and the IR sensor $210_1$ is paired with the IR emitter $215_3$ for eye tracking to detect objects on the right side of the manikin 100. The sequential activation of the sensor/emitter pairs permits independent control of the neck tracking and eye tracking features discussed herein to realistically simulate the simultaneous movement of a human patient's head and eyes to track objects. The manikin 100 also detects when the human-sized body backs away and returns the simulated neck 122 back to a forward-looking orientation.

Once the microprocessor circuit 205 has determined the location of the object with respect to the known locations of the IR sensors $210_{1-N}$, the microprocessor circuit 205 may instruct the neck position sensor 140 to report a current position of the simulated neck 122 within the neck assembly 120. The microprocessor circuit 205 may then compare the current position of the simulated neck 122 with respect to the determined location of the object, and determine whether the current position of the simulated neck 122 corresponds to the determined location of the object. For example, to determine whether the current position of the simulated neck 122 corresponds to the determined location of the object, the microprocessor circuit 205 may determine whether the current position of the simulated neck 122 is oriented towards the determined location of the object. The microprocessor circuit 205 may determine to effect no change in the current position of the simulated neck 122 when it is determined that the current position of both the simulated neck 122 corresponds to the determined location of the object. However, the microprocessor circuit 205 may instruct the neck motor 267 to change the current position of the simulated neck 122 when it is determined that the current position of the simulated neck 122 does not correspond to the determined location of the object. For example, the microprocessor circuit 205 may instruct the neck motor 267 to position the simulated neck 122 such that the simulated neck 122 is oriented (i.e., facing) towards the determined location of the object. The ability of the patient simulator 200 to effect changes in the position of the simulated neck 122 in the horizontal (left and right) directions allows the patient simulator to realistically simulate various medical tests performed by doctors on a human head and neck.

The IR sensors and the IR emitters of the patient simulator 200 may be placed under silicone skin (with special openings) of the manikin 100—this allows the patient simulator 200 to appear more lifelike. In various embodiments, the IR sensors $210_1$ and $210_3$ may be placed above the eye assemblies 101 and 105 and the IR sensor $210_2$ may be placed substantially between the eye assemblies 101 and 105. For example, as shown in FIG. 1, the IR sensors $210_1$ and $210_3$ may be placed in a horizontal plane above the horizontal plane that includes the left and right eye assemblies 101 and 105, and the IR sensor $210_2$ may be placed in a horizontal plane below the horizontal plane that includes the IR sensors $210_1$ and $210_3$. In various embodiments, the IR emitters $215_1$ and $215_2$ may be placed above the eye assemblies 101 and 105, the IR sensor $215_4$ may be placed substantially between the eye assemblies 101 and 105, and the IR emitters $215_3$ and $215_5$ may be placed below the eye assemblies 101 and 105. For example, as shown in FIG. 1, the IR emitters $215_1$ and $215_2$ may be placed in a horizontal plane above the horizontal plane that includes the left and right eye assemblies 101 and 105, the IR emitters $215_3$ and $215_5$ may be placed in a horizontal plane below the horizontal plane that includes the left and right eye assemblies 101 and 105, and the IR sensor $215_4$ may be placed in a horizontal plane below the horizontal plane that includes the IR emitters $215_1$ and $215_2$, and above the horizontal plane that includes the IR emitters $215_3$ and $215_5$. In various embodiments, the eye movement and/or eye tracking is simulated using the IR sensors $210_{1-3}$ and the IR emitters $215_{3-5}$, and the neck movement and/or neck tracking is simulated using the IR sensors $210_{1-3}$ and the IR emitters $215_{1-2}$.

One or more of the three (3) IR sensors $210_{1-3}$ may sense IR response signals originating from one or more of the five (5) IR emitters $215_{1-5}$ to form respective sensor-emitter pairs. For example, in various embodiments, the IR sensors $210_{1-3}$ may be coupled to sense IR response signals resulting from IR emissions from the IR emitters $215_{1-2}$. In addition, or instead, the IR sensors $210_{1-3}$ may be coupled to sense IR response signals resulting from IR emissions from the IR emitters $215_{3-5}$. An IR sensor may be coupled to an IR emitter by tuning the sensing frequency of the IR sensor to the emitting modulated frequency of the IR emitter and/or by positioning the IR sensor in close proximity to the IR emitter. The tuning of the sensing frequency to the emitting modulated frequency results in the IR sensor being isolated from environmental conditions so as to allow accurate sensing of the IR response signal by the IR sensor. Of course, any of the one or more IR sensors may be coupled with any of the one or more IR emitters to effect the movement of the simulated left and right pupils 106 and 107.

Figure 11:
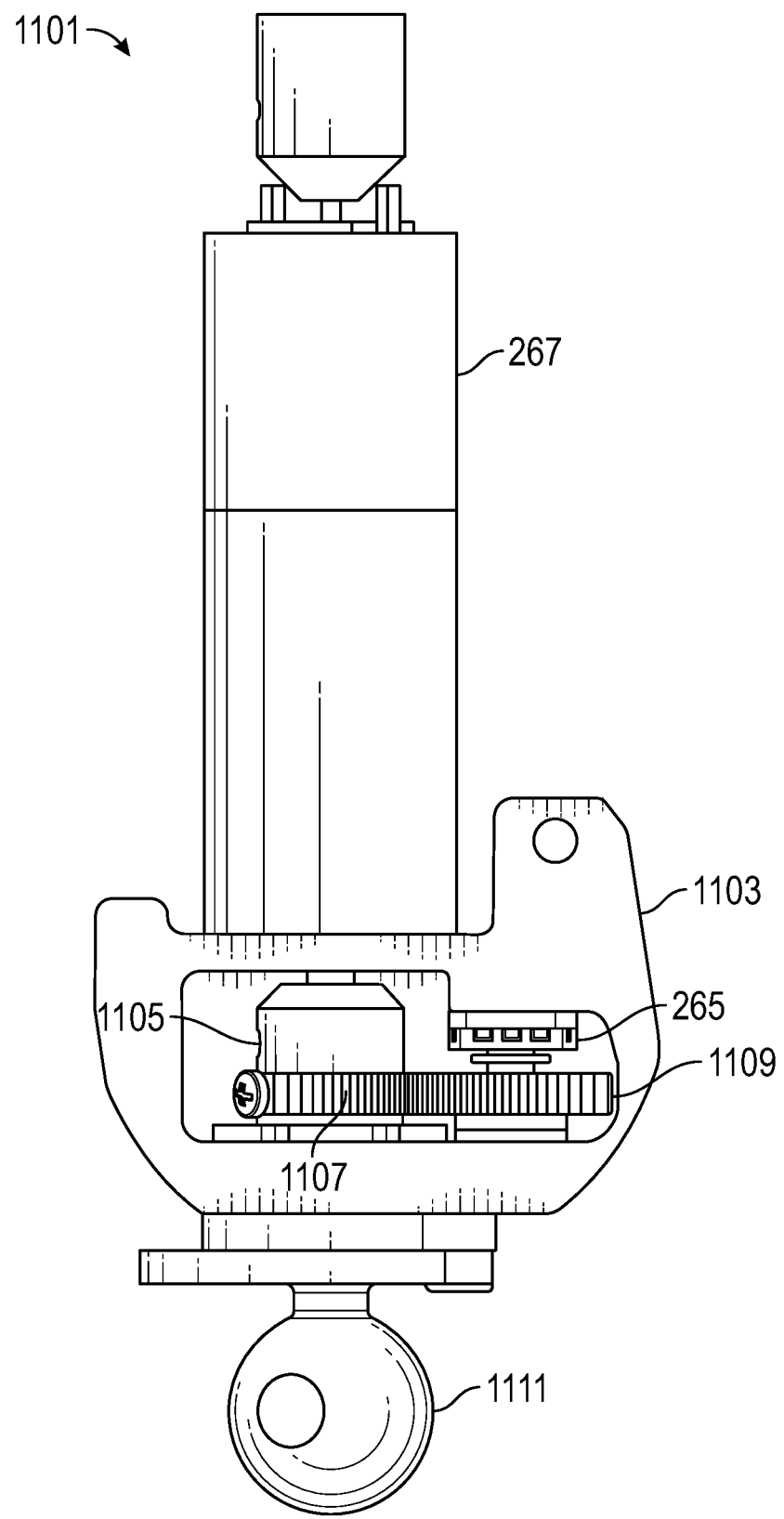
FIG. 11 is an elevational view of a neck assembly, which may be implemented at least in part within the manikin, the patient simulator, and/or the respective environments of FIGS. 1 and 2, according to various embodiments of the present disclosure.
Figure 12:
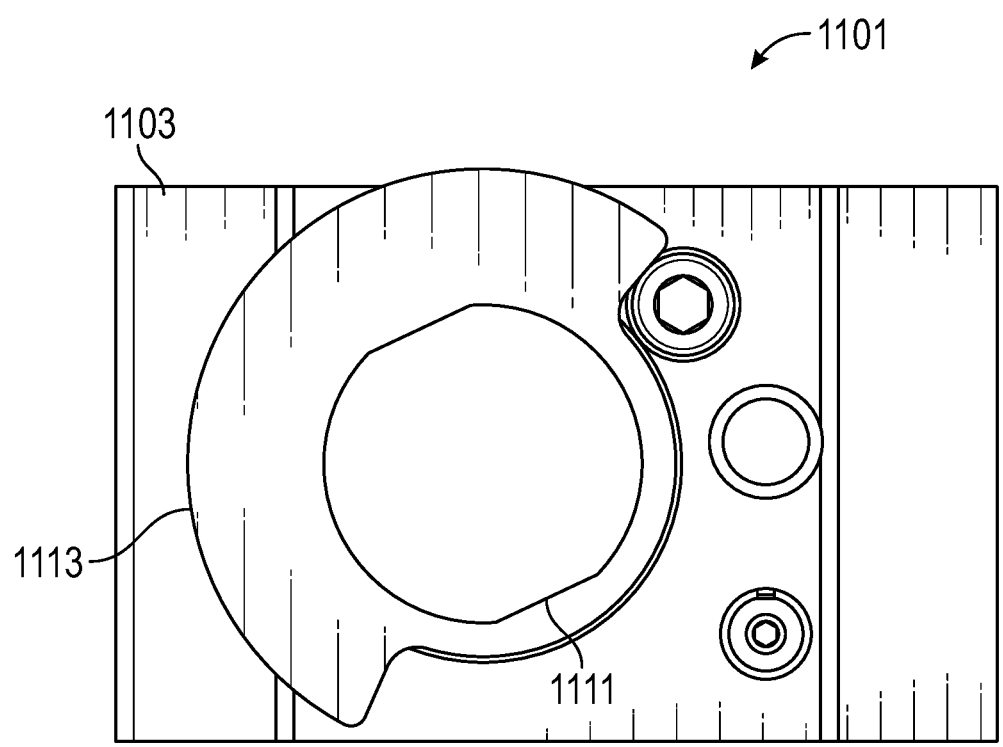
FIG. 12 is a bottom plan view of the neck assembly of FIG. 11, according to various embodiments of the present disclosure.

Turning also to FIGS. 11 and 12, with continuing reference to FIGS. 1 and 2, an exemplary apparatus 1101 used for horizontal (left and right) movement of the simulated neck 122 according to various embodiments of the present disclosure is illustrated. The apparatus 1101 includes the neck position sensor 265, then neck motor 267, a head mount fixture 1103, and a neck joint fixture 1105. In various embodiments, the microprocessor circuit 205 may effect changes in the position of the neck 122 to simulate horizontal (left and right) movements—these movements of the neck 122 in the horizontal direction may be achieved by rotatably mounting the head mount fixture 1103 rotatably to the neck joint fixture 1105. The neck motor 267 may be attached to both the head mount fixture 1103 and the neck joint fixture 1105—for example, a housing of the neck motor 267 may be fixedly attached to the head mount fixture 1103 and a shaft of the neck motor 267 may be fixedly attached to the neck joint fixture 1105. Accordingly, rotation of the shaft of the neck motor 267 causes the head mount fixture 1103 to rotate relative to the neck joint fixture 1105—this relative rotation between the head mount fixture 1103 and the neck joint fixture 1105 effects the realistic neck movement and neck tracking features discussed herein.

The apparatus 1101 may also include indexing gears 1107 and 1109. In various embodiments, the gear 1107 is fixedly attached to the neck joint fixture 1105, and the gear 1109 is rotatably attached to the head mount fixture 1103. The relative rotation between the head mount fixture 1103 and the neck joint fixture 1105 causes the rotating gear 1109 to index around the fixed gear 1107. The neck position sensor 265 is coupled to the rotating gear 1109 to track rotation of the gear 1109 relative to the head mount fixture 1103 during the indexing of the rotating gear 1109 around the fixed gear 1107. In various embodiments, the neck joint fixture 1105 includes a universal joint 1111 that is connectable to a simulated body assembly (not shown) of the patient simulator 200 in a manner that allows manual horizontal and/or vertical movement of the simulated neck 122 independently from rotation of the neck motor 267. Accordingly, the simulated neck 122 may be rotated actively by the neck motor 267 and/or passively by a user in a manner similar to the manner in which a medical professional might rotate a human patient's head or neck (i.e., by pushing against the head). In order to simulate a medical condition called torticollis, the neck motor 267 can be stalled in a position so that the simulated neck 122 can no longer be rotated manually. The neck joint fixture 1105 may also include a flange 1113 to limit the rotational movement of the head mount fixture 1103 relative to the neck joint fixture 1105—in various embodiments, the flange 1113 permits relative rotation of the head mount fixture 1103 by an amount of +/−80 degrees.

The neck motor 267 is electronically connected to the microprocessor circuit 205, which may instruct the neck motor 267 to change the horizontal position of the simulated neck 122. Once so instructed, the neck motor 267 rotates to effect rotational movement of the head mount fixture 1103 relative to the neck joint fixture 1105. Before, during, or after such rotational movement is effected, the microprocessor circuit 205 may also instruct the neck position sensor 265 to report the current position of the head mount fixture 1103 relative to the neck joint fixture 1105 (i.e., the simulated neck 122). Further, the microprocessor circuit 205 may continuously receive electrical signals from the neck position sensor 265 to continuously monitor the position of the simulated neck 122. In various embodiments, the microprocessor circuit 205 may continuously monitor the position of the simulated neck 122 when the neck motion is actuated to realistically simulate the neck movement and neck tracking features discussed herein.

In various embodiments, the neck position sensor 265 discussed herein with respect to sensing the position of the simulated neck 122 may be a rotary potentiometer. The rotary potentiometer may be electro-mechanically connected to the microprocessor circuit 205 and to the shaft of the associated motor discussed herein. The rotary potentiometer may be used as both the divider to obtain adjustable output voltages. As a motor shaft rotates, the wiper (i.e., the sliding contact) of the corresponding rotary potentiometer slides along the resistive body between the terminals of the potentiometer. The sliding of the wiper provides a reading of the adjustable output voltage. The microprocessor circuit 205 monitors the adjustable output voltage, and refers to respective predetermined associations between output voltages and the position of the simulated neck 122 to determine current position. For example, the microprocessor circuit 205 may monitor the adjustable output voltage output by the neck position sensor 265 and refer to a predetermined association between the output voltage of the neck position sensor 265 and the position of the simulated neck 122 to determine a current position of the simulated neck 122. In addition to determining current position, as discussed herein, the microprocessor circuit 205 may also use the monitored adjustable output voltages to confirm that the effected changes in the position of the neck have been accurately effected.

In various embodiments, the patient simulator 200 is capable of detecting a human-sized body approaching or passing the manikin 100 within a range of about 3 feet. If the human-sized body approaches from the side, the manikin 100 will rotate towards the approaching body via the neck assembly 120. However, if the human-sized body approaches from directly in front, the manikin 100 will not rotate via the neck assembly 120 because the manikin 100 is already facing towards the approaching body. The tracking resolution of the neck assembly 120 distinguishes between three different zones of approaching bodies: a left zone, a center zone, and a right zone. If an approaching body is detected in the right zone, the neck motor 267 will turn the simulated neck 122 to the right to face the approaching object. Similarly, if the approaching body is detected in the left zone, the neck motor 267 will turn the simulated neck 122 to the left to face the approaching object. In various embodiments, the neck assembly 120 is capable of rotating about 20 to 30 degrees from left to right. The neck tracking features discussed herein continue to monito the position of the approaching body even after the simulated neck has been turned to the left or right—thus, if the approaching body remains in position, the manikin 100 will continue facing towards the approaching body. The neck movement and neck tracking features discussed herein are operably while the patient simulator 200 is prone on a surface such as a pillow or stretcher. If multiple bodies approach the manikin 100 simultaneously, the neck assembly 120 will turn the simulated neck 122 towards whichever approaching body is closer.

Mouth Movement:

Referring back again to FIG. 2, in various embodiments, to impart vertical (up and down) movement to the simulated mouth 126, the patient simulator 200 includes a mouth motor 270 and (optionally) a mouth position sensor 271. In various embodiments, the mouth motor 270 is a DC gear motor and the mouth position sensor 271 is a Hall Effect sensor. The mouth motor 270 allows control of vertical (up and down) movement of the simulated mouth 126—the vertical control of the simulated mouth 126 is relevant because it allows medical tests to be performed on the simulated mouth 126 (e.g., impaired mouth movement may indicate that the patient has suffered from or is at risk of suffering from trismus), and may contribute to the simulated expression of a clinical response (e.g., pain) by the manikin 100. The mouth position sensor 271 may be a rotary position sensor that senses vertical positions of the simulated mouth 126. In various embodiments, the simulated mouth 126 can also be manually opened and closed by the user. In order to simulate the medical condition of trismus, the mouth motor 270 can be stalled in a position so that the simulated mouth 126 cannot be fully opened. The motion of the simulated mouth 126 may also be synchronized with simulated speech of the patient simulator 200 so that, as the patient simulator 200 speaks, the simulated mouth realistically moves to track the speech. In various embodiments, this speech tracking is accomplished by measuring the envelope of the audio signal sent to the speaker(s) 275 and using an algorithm to open the simulated mouth 126 at the beginning of each speech segment. If the speech segment continues once the simulated mouth 126 has been opened, the simulated mouth 126 continued to follow transitions in the speech envelope. The mouth 126 is closed at the end of the particular speech segment. To simulate the appearance of human speech, the process is then repeated for subsequent speech segments.

More particularly, to simulate the realistic mouth movement features discussed herein, the microprocessor circuit 205 may determine a desired clinical response (e.g., pain) to be simulated by the manikin 100—in various embodiments, the desired clinical response is determined based on one or more user inputs, a predetermined medical training scenario, one or more artificial or sensed external conditions, or any combination thereof. Once the microprocessor circuit 205 has determined the desired clinical response for a given medical training exercise, the microprocessor circuit 205 may instruct the mouth position sensor 271 to report a current position of the simulated mouth 126. The microprocessor circuit 205 may then compare the current position of the simulated mouth 126 with respect to the desired clinical response, and determine whether the current position of the simulated mouth 126 corresponds to the desired clinical response. For example, to determine whether the current position of the simulated mouth 126 corresponds to the desired clinical response, the microprocessor circuit 205 may determine whether the current position of the simulated mouth 126 is oriented (or moving) in accordance with the desired clinical response.

The microprocessor circuit 205 may determine to effect no change in the current position of the simulated mouth 126 when it is determined that the current position of the simulated mouth 126 corresponds to the desired clinical response. However, the microprocessor circuit 205 may instruct the mouth motor 270 to change the current position of the simulated mouth 126 when it is determined that the current position of the simulated mouth 126 does not correspond to the desired clinical response. For example, the microprocessor circuit 205 may instruct the mouth motor 270 to position the simulated mouth 126 such that the simulated mouth 126 is oriented in accordance with the desired clinical response. In various embodiments, the microprocessor circuit 205 may change the positions of the simulated mouth 126 in the vertical (up and down) direction. The ability of the patient simulator 200 to effect changes in the position of the simulated mouth 126 in the vertical (up and down) direction allows the patient simulator to realistically simulate various medical tests performed by doctors on human mouths, and contributes at least partially to the expression of the desired clinical response (e.g., pain) by the manikin 100.

Figure 13:
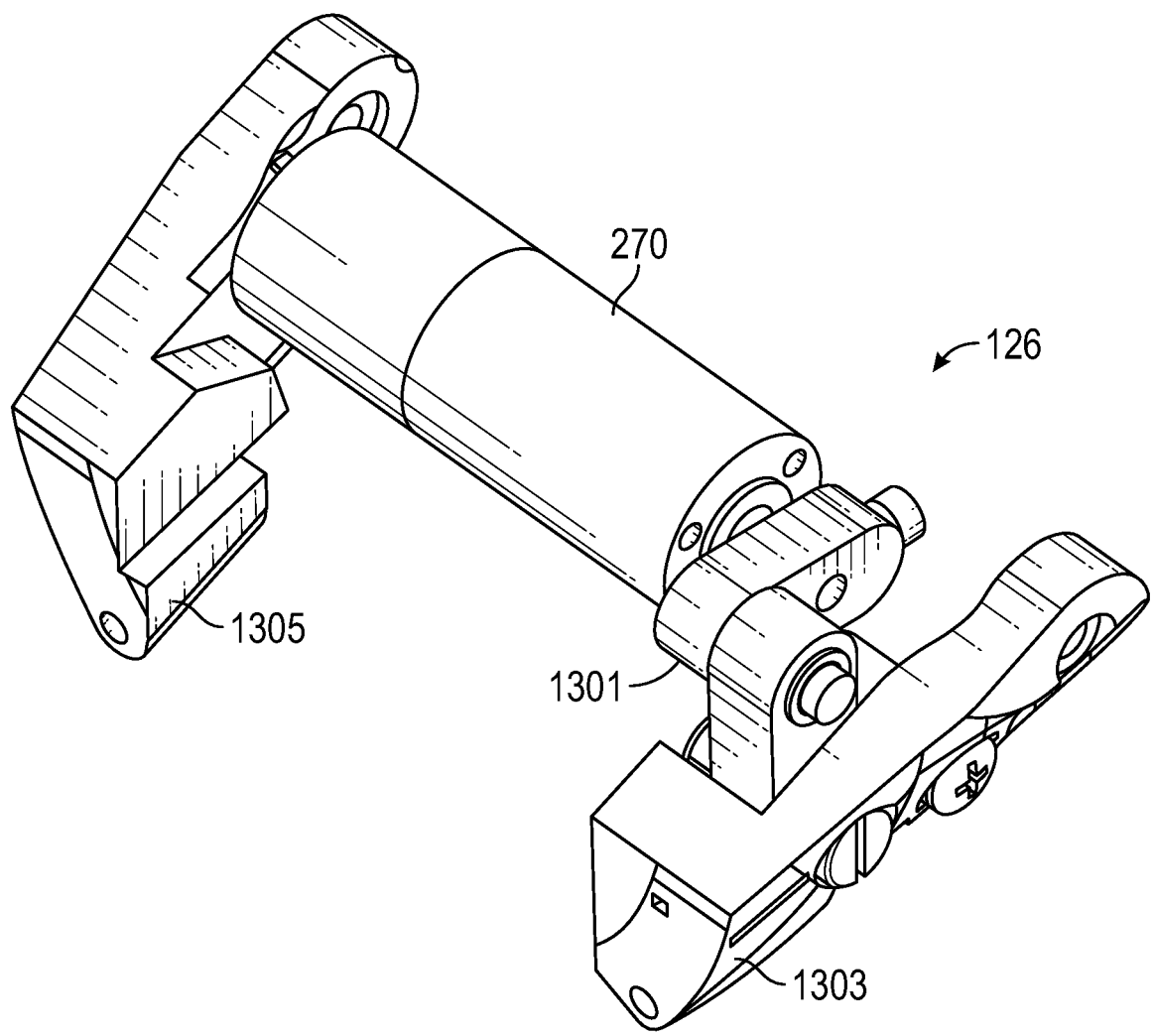
FIG. 13 is a perspective view of a mouth assembly, which may be implemented at least in part within the manikin, the patient simulator, and/or the respective environments of FIGS. 1 and 2, according to various embodiments of the present disclosure.

Turning also to FIG. 13, with continuing reference to FIGS. 1 and 2, in various embodiments, the mouth motor 270 is attached to a linkage 1301 (e.g., a four-bar linkage) capable of relaying the torque of the mouth motor 270 to a pair of rotatable hinge parts 1303 and 1305. The rotatable hinge parts 1303 and 1305 may be joined by a curved mandible part (not shown)—in combination, the rotatable hinge parts 1303 and 1305 and the curved mandible part may be covered by silicone material serving as at least a portion of the simulated mouth 126 of the manikin 100. Accordingly, when the microprocessor circuit 205 operates the mouth motor 270 to rotate, the linkage 1301 relays the torque to the two rotatable hinge parts 1303 and 1305 (i.e., the simulated mouth 126) to simulate human mouth motion (e.g., human speech).

In those embodiments in which a mouth position sensor 271 is included, the microprocessor circuit 205 may instruct the mouth position sensor 271 to report the current position of the two rotatable hinge parts 1303 and 1305 (i.e., the simulated mouth 126). Further, the microprocessor circuit 205 may continuously receive electrical signals from the mouth position sensor 271 to continuously monitor the position of the simulated mouth 126. In various embodiments, the microprocessor circuit 205 may continuously monitor the position of the simulated mouth 126 when the mouth motion is actuated between open and closed positions. During the monitoring, when the microprocessor circuit 205 determines that the simulated mouth 126 has reached the closed position, the microprocessor circuit 205 may emit electrical signals to reverse the rotation of the mouth motor 270 so that the simulated mouth 126 is actuated to the open position.

In various embodiments, the mouth position sensor 271 discussed herein with respect to sensing the position of the simulated mouth 126 may be a rotary potentiometer. The rotary potentiometer may be electro-mechanically connected to the microprocessor circuit 205 and to the shaft of the associated motor discussed herein. The rotary potentiometer may be used as both the divider to obtain adjustable output voltages. As a motor shaft rotates, the wiper (i.e., the sliding contact) of the corresponding rotary potentiometer slides along the resistive body between the terminals of the potentiometer. The sliding of the wiper provides a reading of the adjustable output voltage. The microprocessor circuit 205 monitors the adjustable output voltage, and refers to respective predetermined associations between output voltages and the position of the simulated mouth 126 to determine current position. For example, the microprocessor circuit 205 may monitor the adjustable output voltage output by the mouth position sensor 271 and refer to a predetermined association between the output voltage of the mouth position sensor 271 and the position of the simulated mouth 126 to determine a current position of the simulated mouth 126. In addition to determining current position, as discussed herein, the microprocessor circuit 205 may also use the monitored adjustable output voltages to confirm that the effected changes in the position of the mouth have been accurately effected.

Speech Recognition:

Referring back again to FIG. 2, in various embodiments, the patient simulator 200 includes a microphone 280 capable of registering voices or other sounds up to about 6 feet from the manikin 100. The patient simulator 200 can then response to the voice either verbally (through the speaker(s) 275) and/or by moving one or more of the herein described components of the manikin 100. In various embodiments, the patient simulator 200 may include a Wi-Fi module (not shown) in communication with the microprocessor circuit 205 (via, for example, the I/O interface 225). The microphone 280 constantly streams received audio data to the microprocessor circuit 205, which searches for voice-like segments within the audio data. If such voice-like segment(s) are detected, the microprocessor circuit 205 sends the segment(s) via the Wi-Fi module to, for example, a cloud-based voice recognition application programming interface (API). The cloud-based API replies to the Wi-Fi module with the text extracted from the audio file. The microprocessor circuit 205 then parses this text to determine the manner in which to react to the voice command. In response to the voice command, the patient simulator 200 may respond verbally through the speaker(s) 275, or may respond by moving one or more of the various components of the manikin discussed herein. For example, if the voice command says "how old are you?" the patient simulator 200 may respond verbally through the speaker(s) 275 with "I am five years old." For another example, if the voice command says "close your eyes" the patient simulator 200 will move the simulated left and right eyelids 108 and 109 to their respective closed positions.

Operational Routines:

Due to the various features and components discussed herein, the manikin 100 is capable of rotating the simulated neck 122 in a horizontal (left and right) direction, opening and closing the simulated mouth 126 in a vertical (up and down) direction, raising and lowering the simulated left and right brows 117 and 118 in a vertical (up and down) direction, opening and closing the simulated left and right eyelids 108 and 109 in a vertical (up and down) direction, moving the simulated left and right pupils 106 and 107 in horizontal (left and right) and vertical (up and down) directions, constricting and dilating the simulated left and right irises 601 and 603, and activating the tear duct assembly 110 to simulate life-like human tear production. Each of these motions is controlled by the microprocessor circuit 205 (or another controller) of the patient simulator 200, which may be embedded in the manikin 100 on a printed circuit board (PCB) or located elsewhere. In various embodiments, electrical power is provided to the various motors and other components of the patient simulator 200 using batteries embedded in the manikin 100 or the simulated body (not shown) of the patient simulator 200.

In various embodiments, high resolution control of the patient simulator 200's various motors 231, 233, 236, 238, 244, 249, 252, 255, 261, 263, and 267 allows each of the corresponding simulated body parts to be (independently) moved to many different positions within a particular range of motion (e.g., a range of motion similar to that of a typical human). Thus, motion speed and range of motion can be customized during manufacture of the patient simulator 200, or by the user during use. Some motion may be pre-programmed into the microprocessor circuit 205, other motion may be pseudo-randomly generated by the microprocessor circuit 205, and still other motion may be generated in response to user interaction with the manikin 100. The various motions of the manikin 100 may be combined simultaneously to simulate life-like human facial features/expressions, such as, for example, a pain grimace or other emotional or clinical response. During a human pain grimace, the mouth closes tightly, the neck twists to the side, the eyes close and the brows furrow (or lower)—the manikin 100 is capable of mimicking all of these motions simultaneously in real time. Other emotional or clinical responses can also be mimicked using the patient simulator 200 (which may be implemented at least in part within the environment and/or the manikin 100).

In addition to realistically mimicking emotional or clinical responses, an idle control routine can be implemented by the patient simulator 200 (which may be implemented at least in part within the environment and/or the manikin 100) to make the manikin 100 look more life-like by, for example, expressing varying levels of anxiety using one or more of the motions/features discussed herein. The idle control routine controls the various components and features of the manikin 100 when the patient simulator 200 is not acting out some other command—the user can toggle a computer input device such as the keyboard, mouse, or joystick connected through the I/O interface 225 to select from a list of varying anxiety levels. For example, the user can select "anxious" or "normal" to indicate the anxiety level of the patient simulator 200 (which may be implemented at least in part within the environment and/or the manikin 100). The normal state will cause the various motions and features of the manikin 100 to move in a manner typical of a calm or relaxed person. On the other hand, the "anxious" state may cause the various motions and features of the manikin 100 to be exaggerated and/or to move more rapidly. In various embodiments, these routines (or others) control one or more of the simulated neck 122, the simulated mouth 126, the simulated left and right brows 117 and 118, the simulated left and right eyelids 108 and 109, the simulated left and right pupils 106 and 107, the simulated left and right irises 601 and 603, and the tear duct assembly 110 to simulate life-like human anxiety levels.

The microprocessor circuit 205 may pseudo-randomly generate a position for each of these components, and may also pseudo-randomly generate a time interval for such position to be held before another position is generated. Once a position has been generated, the microprocessor circuit 205 sends electrical signals to one or more of the various motors 231, 233, 236, 238, 244, 249, 252, 255, 261, 263, and 267 to move the corresponding body part(s) to the appropriate position(s). At higher anxiety levels, the range of motion for each component of the manikin 100 may be expanded, and the time interval between movements may be shortened—this creates an overall effect that realistically simulates the appearance of a life-like human in a clinical setting (e.g., waiting in a hospital bed). For example, the manikin 100 may look around occasionally with both the simulated neck 122 and the simulated left and right pupils 106 and 107, the manikin 100 may yawn occasionally with the simulated mouth 126, the manikin 100 may blink with the simulated left and right eyelids 108 and 109, and the manikin may occasionally furrow the simulated left and right brows 117 and 118.

In addition to the above-discussed routines, the patient simulator 200 (which may be implemented at least in part within the environment and/or the manikin 100) is configured to allow direct, real-time control of the positioning or activation of the various motions and features of the manikin 100 discussed herein, including at least one or more of the following components: the tear duct assembly 110, the simulated left and right pupils 106 and 107, the simulated left and right eyelids 108 and 109, the simulated left and right brows 117 and 118, the simulated neck 122, the simulated mouth 126, the simulated left and right irises 601 and 603. Such direct, real-time control may be implemented using computer input devices, such as, the keyboard, mouse, or joystick connected through the I/O interface 225. For example, the user may move the simulated left and right pupils 106 and 107 to any position that is a normal human lifelike position. In various embodiments, a graphical display may be presented to the user on the display connected through the I/O interface 225. The graphical display may depict an eye with a pupil and an iris. In various embodiments, a user may control the positioning of the simulated left and right pupils 106 and 107 on the patient simulator by controlling the position of the pupil of the graphical eye. The user may control the pupil of the graphical eye by moving the mouse cursor or the joystick to change the position of the pupil of the graphical eye, and thereby allow the microprocessor circuit 205 to effect movement of the simulated left pupil 106, the simulated right pupil 107, or both. The user may also use a finger or stylus on a touch screen display and control the pupil of the graphical eye to change the position of the simulated left pupil 106, the simulated right pupil 107, or both.

As the cursor/joystick/finger moves, the microprocessor circuit 205 receives the electrical signals associated with these movements through the I/O interface 225, and effects corresponding movements of the simulated left and right pupils 106 and 107. For example, a computer or processor connected to the cursor/joystick/finger provides the location of the cursor/joystick/finger in reference to the pupil of the graphical eye, and the microprocessor circuit 205 converts the location of the pupil to the corresponding simulator positions of the simulated left and right pupils 106 and 107. The microcontroller may employ a pre-stored map having locations on the display screen depicting the graphical eye plotted to corresponding locations of the simulated left and right pupils 106 and 107 on the patient simulator. In various embodiments, when the cursor/joystick/finger is moved outside the graphical eye, the simulated left and right pupils 106 and 107 may be positioned in their default positions.

The microprocessor circuit 205 is configured to effect movements of the tear duct assembly 110, the simulated left and right pupils 106 and 107, the simulated left and right eyelids 108 and 109, the simulated left and right brows 117 and 118, the simulated neck 122, the simulated mouth 126, and/or the simulated left and right irises 601 and 603 in real-time either independently or together with respect to each other. The system may also include pre-programmed patterns to simulate various patient scenarios. The system may also be configured to allow combinations of real-time control via cursor, joystick or other input with the pre-programmed patterns. For example, the pre-programmed pattern may continue until a control input for a real-time control is received. Similarly, the system may also be configured to allow combinations of object tracking with the pre-programmed patterns. For example, the pre-programmed pattern may continue until a tracking object is detected by one of the sensors and/or an input for object tracking is received from a user.

In various embodiments, the patient simulator 200 (which may be implemented at least in part within the environment and/or the manikin 100) includes one or more features as provided in medical simulators provided by Gaumard Scientific Company, Inc. based out of Miami, Fla., including but not limited to the following models: S1000 Hal®, S1020 Hal®, S1030 Hal®, S3000 Hal®, S2000 Susie®, S221 Clinical Chloe®, S222 Clinical Chloe®, S222.100 Super Chloe®, S303 Code Blue®, S304 Code Blue®, S100 Susie®, S100 Simon®, S200 Susie®, S200 Simon®, S201 Susie®, S201 Simon®, S203 Susie®, S204 Simon®, S205 Simple Simon®, S206 Simple Susie®, S3004 Pediatric Hal®, S3005 Pediatric Hal®, S3009 Premie Hal®, S3010 Newborn Hal®, S110 Mike®, S110 Michelle®, S150 Mike®, S150 Michelle®, S107 Multipurpose Patient Care and CPR Infant Simulator, S117 Multipurpose Patient Care and CPR Pediatric Simulator, S157 Multipurpose Patient Care and CPR Pediatric Simulator, S575 Noelle®, S565 Noelle®, S560 Noelle®, S555 Noelle®, S550 Noelle®, S550.100 Noelle®, S2200 Victoria®, S2220 Super Tory®, and/or other patient simulators.

In a first aspect, the present disclosure introduces a patient simulator, including a neck assembly including a simulated neck; one or more infrared (IR) emitters configured to emit IR radiation towards an object placed in front of the patient simulator; one or more IR sensors configured to receive an IR response signal reflected off of the object; and a microprocessor configured to determine a location of the object based on the sensing of the IR response signal by the one or more IR sensors, and to effect movement of the simulated neck based on the determined location of the object. In various embodiments, to effect movement of the simulated neck, the microprocessor is configured to compare a current position of the simulated neck with the determined location of the object. In various embodiments, the neck assembly further includes a neck position sensor configured to sense a position of the simulated neck, and to provide a first electrical signal to the microprocessor based on the sensed position of the simulated neck; and a neck motor configured to receive a second electrical signal from the microprocessor to move the simulated neck. In various embodiments, to effect movement of the simulated neck, the microprocessor is configured to receive the first electrical signal from the neck position sensor, to determine the second electrical signal based at least in part on the first electrical signal, and to provide the second electrical signal to the neck motor. In various embodiments, the patient simulator further includes a left eye assembly including a simulated left pupil, and a right eye assembly including a simulated right pupil; wherein the microprocessor is further configured to effect movement of the simulated left pupil and/or the simulated right pupil based on the determined location of the object. In various embodiments, to effect movement of the simulated neck, the microprocessor is configured to compare a current position of the simulated neck with the determined location of the object; and, to effect movement of the simulated left pupil and/or the simulated right pupil, the microprocessor is configured to compare a current position of the simulated left pupil and/or the simulated right pupil with the determined location of the object. In various embodiments, the microprocessor is configured to effect movement of the simulated neck by a first displacement amount, and to effect movement of the simulated left pupil and/or the simulated right pupil by a second displacement amount, the first displacement amount being different from the second displacement amount. In various embodiments, at least one of the one or more IR emitters is configured to emit the IR radiation in a burst of frequency modulated pulses, and at least one of the one or more IR sensors is configured to record a value corresponding to an intensity of the IR response signal.

In a second aspect, the present disclosure introduces a method, including emitting, via one or more infrared (IR) emitters, IR radiation toward an object placed in front of a patient simulator, the patient simulator including a neck assembly having a simulated neck; sensing, via one or more IR sensors, an IR response signal caused by the IR radiation being reflected off of the object; determining, using a microprocessor, a location of the object based on the sensing of the IR response signal by the one or more IR sensors; and effecting, using the microprocessor, movement of the simulated neck based on the determined location of the object. In various embodiments, effecting movement of the simulated neck using the microprocessor includes comparing a current position of the simulated neck with the determined location of the object. In various embodiments, the method further includes sensing, using a neck position sensor of the neck assembly, a position of the simulated neck; providing, using the neck position sensor, a first signal to the microprocessor based on the sensed position of the simulated neck; and receiving, using a neck motor of the neck assembly, a second electrical signal from the microprocessor to move the simulated neck. In various embodiments, effecting movement of the simulated neck with the microprocessor includes receiving the first electrical signal from the neck position sensor; determining the second electrical signal based at least in part on the first electrical signal; and providing the second electrical signal to the neck motor. In various embodiments, the patient simulator further includes a left eye assembly including a simulated left pupil, and a right eye assembly including a simulated right pupil; and the method further includes effecting, using the microprocessor, movement of the simulated left pupil and/or the simulated right pupil based on the determined location of the object. In various embodiments, effecting movement of the simulated neck using the microprocessor includes comparing a current position of the simulated neck with the determined location of the object; and effecting movement of the simulated left pupil and/or the simulated right pupil using the microprocessor including comparing a current position of the simulated left pupil and/or the simulated right pupil with the determined location of the object. In various embodiments, the method further includes effecting, using the microprocessor, movement of the simulated neck by a first displacement amount, and effecting, using the microprocessor, movement of the simulated left pupil and/or the simulated right pupil by a second displacement amount; wherein the first displacement amount is different from the second displacement amount. In various embodiments, at least one of the one or more IR emitters emits the IR radiation in a burst of frequency modulated pulses, and at least one of the one or more IR sensors records a value corresponding to an intensity of the IR response signal.

In a third aspect, the present disclosure introduces a patient simulator, including a left brow assembly, including a simulated left brow and a left brow position sensor configured to sense a position of the simulated left brow, and to provide a first electrical signal based on the sensed position; a right brow assembly including a simulated right brow and a right brow position sensor configured to sense a position of the simulated right brow, and to provide a second electrical signal based on the sensed position; and a microprocessor configured to move the simulated left brow based at least in part on the first electrical signal, and to move the simulated right brow based at least in part on the second electrical signal. In various embodiments, the patient simulator further includes a left brow motor configured to receive a third electrical signal to move the simulated left brow, and a right brow motor configured to receive a fourth electrical signal to move the simulated right brow. In various embodiments, the patient simulator further includes a left Bowden cable operably coupling the left brow motor to the simulated left brow, and a right Bowden cable operably coupling the right brow motor to the simulated right brow. In various embodiments, the microprocessor is configured to receive the first and second electrical signals from the respective left and right brow position sensors, to determine the third and fourth electrical signals based at least in part on the respective first and second electrical signals, and to provide the third and fourth electrical signals to the respective left and right brow motors. In various embodiments, each of the simulated left brow and the simulated right brow is configured to move in a vertical direction. In various embodiments, the microprocessor is configured to effect movement of the simulated left brow jointly with respect to the movement of the simulated right brow. In various embodiments, the microprocessor is configured to effect movement of the simulated left brow independently with respect to movement of the simulated right brow. In various embodiments, the microprocessor is configured to effect movement of the simulated left brow by a first displacement amount, and to effect movement of the simulated right brow by a second displacement amount, the first displacement amount being different from the second displacement amount.

In a fourth aspect, the present disclosure introduces a method, including sensing, using a left brow position sensor, a position of a simulated left brow of a patient simulator; sensing, using a right brow position sensor, a position of a simulated right brow of the patient simulator; providing, based on the sensed position of the simulated left brow, a first electrical signal; providing, based on the sensed position of the simulated right brow, a second electrical signal; moving, using a microprocessor and based at least in part on the first electrical signal, the simulated left brow; and moving, using the microprocessor and based at least in part on the second electrical signal, the simulated right brow. In various embodiments, the method further includes receiving, using a left brow motor, a third electrical to move the simulated left brow; and receiving, using a right brow motor, a fourth electrical signal to move the simulated right brow. In various embodiments, moving the simulated left brow includes effecting, using the left brow motor, movement of a left Bowden cable operably coupled to the simulated left brow; and moving the simulated right brow includes effecting, using the right brow motor, movement of a right Bowden cable operably coupled to the simulated right brow. In various embodiments, the microprocessor receives the first and second electrical signals from the respective left and right brow position sensors, determines the third and fourth electrical signals based at least in part on the respective first and second electrical signals, and provides the third and fourth electrical signals to the respective left and right brow motors. In various embodiments, each of the simulated left brow and the simulated right brow moves in a vertical direction. In various embodiments, the microprocessor effects movement of the simulated left brow jointly with respect to the movement of the simulated right brow. In various embodiments, the microprocessor effects movement of the simulated left brow independently with respect to movement of the simulated right brow. In various embodiments, the method further includes effecting, using the microprocessor, movement of the simulated left brow by a first displacement amount; and effecting, using the microprocessor, movement of the simulated right brow by a second displacement amount; wherein the first displacement amount being different from the second displacement amount.

In a fifth aspect, the present disclosure introduces a patient simulator, including a manikin in the form of a human face, the manikin including a first simulated cheek and a first artificial pore extending from an interior of the first simulated cheek to an exterior of the first simulated cheek; a first pump configured receive a first electrical signal to communicate fluid to the interior of the first simulated cheek and through the first artificial pore so that said fluid beads on the exterior of the first simulated cheek to simulate the production of a realistic human tear; and a microprocessor configured provide the first electrical signal to the first pump. In various embodiments, the patient simulator further includes a fluid chamber formed into the interior of the first simulated cheek adjacent the first artificial pore. In various embodiments, the patient simulator further includes a fitting connected to the interior of the first simulated cheek adjacent the fluid chamber. In various embodiments, the patient simulator further includes a fluid reservoir from which the first pump is configured to draw fluid to communicate to the interior of the first simulated cheek. In various embodiments, the first pump is a peristaltic pump. In various embodiments, the first simulated cheek includes one or more layers of silicone skin. In various embodiments, the first artificial pore is formed in the first simulated cheek by passing a thin needle having a diameter of approximately 0.05 inches through the one or more layers of silicone skin. In various embodiments, the manikin further includes a second simulated cheek and a second artificial pore extending from an interior of the second simulated cheek to an exterior of the second simulated cheek; the patient simulator further includes a second pump configured receive a second electrical signal to communicate fluid to the interior of the second simulated cheek and through the second artificial pore so that said fluid beads on the exterior of the second simulated cheek to simulate the production of a realistic human tear; and the microprocessor is configured provide the second electrical signal to the second pump.

In a sixth aspect, the present disclosure introduces a method, including providing a manikin in the form of a human face, the manikin including a first simulated cheek and a first artificial pore extending from an interior of the first simulated cheek to an exterior of the first simulated cheek; receiving, using a first pump, a first electrical signal; communicating, using the first pump and based at least in part on the first electrical signal, a fluid to the interior of the first simulated cheek and through the first artificial pore so that said fluid beads on the exterior of the first simulated cheek to simulate the production of a realistic human tear; and providing, using a microprocessor, the first electrical signal to the first pump. In various embodiments, the manikin includes a fluid chamber formed into the interior of the first simulated cheek adjacent the first artificial pore. In various embodiments, the manikin includes a fitting connected to the interior of the first simulated cheek adjacent the fluid chamber. In various embodiments, communicating the fluid to the interior of the first simulated cheek using the pump includes drawing the fluid from a fluid reservoir and pumping the fluid to the interior of the first simulated cheek. In various embodiments, the first pump is a peristaltic pump. In various embodiments, the first simulated cheek includes one or more layers of silicone skin. In various embodiments, the first artificial pore is formed in the first simulated cheek by passing a thin needle having a diameter of approximately 0.05 inches through the one or more layers of silicone skin. In various embodiments, the manikin further includes a second simulated cheek and a second artificial pore extending from an interior of the second simulated cheek to an exterior of the second simulated cheek; and the method further includes receiving, using a second pump, a second electrical signal; communicating, using the second pump and based at least in part on the second electrical signal, fluid to the interior of the second simulated cheek and through the second artificial pore so that said fluid beads on the exterior of the second simulated cheek to simulate the production of a realistic human tear; and providing, using the microprocessor, the second electrical signal to the second pump.

In a seventh aspect, the present disclosure introduces a patient simulator, including a fluid reservoir including an expandable vessel configured to lengthen as fluid is filled into the fluid reservoir, and to shorten as fluid is emptied from the fluid reservoir; an infrared (IR) emitter configured to emit IR radiation towards the expandable vessel; an IR sensor configured to receive an IR response signal reflected off of the expandable vessel; and a microprocessor configured to determine a length of the expandable vessel based at least in part on the sensing of the IR response signal by the IR sensor, and to calculate, based at least in part on the determined length, an amount of fluid contained within the fluid reservoir. In various embodiments, the fluid reservoir includes one or more sidewalls to prevent, or at least reduce, leaning of the expandable vessel as the expandable vessel lengthens and shortens. In various embodiments, the sidewalls are made of a material having a higher IR absorptivity than that of the expandable vessel so as to prevent, or at least reduce, measurement errors by the IR sensor. In various embodiments, the fluid reservoir includes a housing to which the expandable vessel is fixed so that lengthening of the expandable vessel occurs in a single direction. In various embodiments, the amount of lengthening or shortening of the expandable vessel is correlated to a change in the amount of fluid contained within the fluid reservoir. In various embodiments, the IR emitter is configured to emit the IR radiation in a burst of frequency modulated pulses, and the IR sensor is configured to record a value corresponding to an intensity of the IR response signal. In various embodiments, the patient simulator further includes a pump configured to communicate fluid from the fluid reservoir to a manikin in the form of a human face so that said fluid beads to simulate the production of a realistic human tear. In various embodiments, the pump is electronically connected to the microprocessor and fluidically connected to the manikin.

In an eighth aspect, the present disclosure introduces a method, including changing a length of an expandable vessel of a fluid reservoir as fluid is filled into, or emptied from, the fluid reservoir; emitting, via an infrared (IR) emitter, IR radiation towards the expandable vessel; sensing, via an IR sensor, an IR response signal caused by the IR radiation being reflected off of the expandable vessel; determining, using a microprocessor, a length of the expandable vessel based at least in part on the sensing of the IR response signal by the IR sensor; and calculating, using the microprocessor and based at least in part on the determined length, an amount of fluid contained within the fluid reservoir. In various embodiments, the method further includes preventing, or at least reducing, using one or more sidewalls of the fluid reservoir, leaning of the expandable vessel as the length of the expandable vessel changes. In various embodiments, the sidewalls are made of a material having a higher IR absorptivity than that of the expandable vessel so as to prevent, or at least reduce, measurement errors by the IR sensor. In various embodiments, the fluid reservoir includes a housing to which the expandable vessel is fixed so that lengthening of the expandable vessel occurs in a single direction. In various embodiments, the changing of the length of the expandable vessel is correlated to a change in the amount of fluid contained within the fluid reservoir. In various embodiments, the method further includes emitting, using the IR emitter, the IR radiation in a burst of frequency modulated pulses, and recording, using the IR sensor, a value corresponding to an intensity of the IR response signal. In various embodiments, the method further includes communicating, using a pump, fluid from the fluid reservoir to a manikin in the form of a human face so that said fluid beads to simulate the production of a realistic human tear. In various embodiments, the pump is electronically connected to the microprocessor and fluidically connected to the manikin.

It is understood that variations may be made in the foregoing without departing from the scope of the present disclosure.

In various embodiments, the elements and teachings of the various embodiments may be combined in whole or in part in some or all of the various embodiments. In addition, one or more of the elements and teachings of the various embodiments may be omitted, at least in part, and/or combined, at least in part, with one or more of the other elements and teachings of the various embodiments.

In various embodiments, while different steps, processes, and procedures are described as appearing as distinct acts, one or more of the steps, one or more of the processes, and/or one or more of the procedures may also be performed in different orders, simultaneously and/or sequentially. In various embodiments, the steps, processes and/or procedures may be merged into one or more steps, processes and/or procedures.

In various embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Although various embodiments have been described in detail above, the embodiments described are illustrative only and are not limiting, and those skilled in the art will readily appreciate that many other modifications, changes and/or substitutions are possible in the various embodiments without materially departing from the novel teachings and advantages of the present disclosure. Accordingly, all such modifications, changes, and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112, paragraph 6 for any limitations of any of the claims herein, except for those in which the claim expressly uses the word "means" together with an associated function.

What is claimed is:

1. A patient simulator configured to physically simulate a life-like human emotional response, the patient simulator comprising:
    a manikin in the form of a human face, the manikin including a first simulated cheek and a first artificial pore extending from an interior of the first simulated cheek to an exterior of the first simulated cheek;
    a first pump configured receive a first electrical signal to communicate fluid to the interior of the first simulated cheek and through the first artificial pore so that said fluid beads on the exterior of the first simulated cheek to simulate the production of a realistic human tear; and
    a microprocessor configured to provide the first electrical signal to the first pump.

2. The patient simulator of claim 1, further comprising a fluid chamber formed into the interior of the first simulated cheek adjacent the first artificial pore.

3. The patient simulator of claim 2, further comprising a fitting connected to the interior of the first simulated cheek adjacent the fluid chamber.

4. The patient simulator of claim 1, further comprising a fluid reservoir from which the first pump is configured to draw fluid to communicate to the interior of the first simulated cheek.

5. The patient simulator of claim 1, wherein the first pump is a peristaltic pump.

6. The patient simulator of claim 1, wherein the first simulated cheek comprises one or more layers of silicone skin.

7. The patient simulator of claim 6, wherein the first artificial pore is formed in the first simulated cheek by passing a thin needle having a diameter of approximately 0.05 inches through the one or more layers of silicone skin.

8. The patient simulator of claim 1,
    wherein the manikin further includes a second simulated cheek and a second artificial pore extending from an interior of the second simulated cheek to an exterior of the second simulated cheek;
    wherein the patient simulator further comprises a second pump configured receive a second electrical signal to communicate fluid to the interior of the second simulated cheek and through the second artificial pore so that said fluid beads on the exterior of the second simulated cheek to simulate the production of a realistic human tear; and
    wherein the microprocessor is configured provide the second electrical signal to the second pump.

9. The patient simulator of claim 1, further comprising:
    a fluid chamber formed into the interior of the first simulated cheek adjacent the first artificial pore; and
    a fitting connected to the interior of the first simulated cheek adjacent the fluid chamber;
    wherein the first pump is configured to communicate the fluid via the fitting to the fluid chamber formed into the interior of the first simulated cheek and through the first artificial pore.

10. A method, comprising:
    physically simulating, using a patient simulator, a life-like human emotional response, wherein physically simulating the life-like human emotional response comprises:
        providing the patient simulator in the form of a human face, the patient simulator including a first simulated cheek and a first artificial pore extending from an interior of the first simulated cheek to an exterior of the first simulated cheek;
        receiving, using a first pump, a first electrical signal;
        communicating, using the first pump and based at least in part on the first electrical signal, a fluid to the interior of the first simulated cheek and through the first artificial pore so that said fluid beads on the exterior of the first simulated cheek to simulate the production of a realistic human tear; and
        providing, using a microprocessor, the first electrical signal to the first pump.

11. The method of claim 10, wherein the patient simulator includes a fluid chamber formed into the interior of the first simulated cheek adjacent the first artificial pore.

12. The method of claim 11, wherein the patient simulator includes a fitting connected to the interior of the first simulated cheek adjacent the fluid chamber.

13. The method of claim 10, wherein communicating the fluid to the interior of the first simulated cheek using the pump comprises drawing the fluid from a fluid reservoir and pumping the fluid to the interior of the first simulated cheek.

14. The method of claim 10, wherein the first pump is a peristaltic pump.

15. The method of claim 10, wherein the first simulated cheek comprises one or more layers of silicone skin.

16. The method of claim 15, wherein the first artificial pore is formed in the first simulated cheek by passing a thin needle having a diameter of approximately 0.05 inches through the one or more layers of silicone skin.

17. The patient simulator of claim 10,
    wherein the manikin further includes a second simulated cheek and a second artificial pore extending from an interior of the second simulated cheek to an exterior of the second simulated cheek;
    wherein the method further comprises:
        receiving, using a second pump, a second electrical signal;
        communicating, using the second pump and based at least in part on the second electrical signal, a fluid to the interior of the second simulated cheek and through the second artificial pore so that said fluid beads on the exterior of the second simulated cheek to simulate the production of a realistic human tear; and
        providing, using the microprocessor, the second electrical signal to the second pump.

18. The method of claim 10,
    wherein the patient simulator further includes:
        a fluid chamber formed into the interior of the first simulated cheek adjacent the first artificial pore; and a fitting connected to the interior of the first simulated cheek adjacent the fluid chamber;
and
wherein communicating, using the first pump and based at least in part on the first electrical signal, a fluid to the interior of the first simulated cheek and through the first artificial pore comprises communicating the fluid via the fitting to the fluid chamber formed into the interior of the first simulated cheek and through the first artificial pore.

* * * * *